(12) United States Patent
Sigurdsson et al.

(10) Patent No.: US 12,251,327 B2
(45) Date of Patent: *Mar. 18, 2025

(54) SUPPORT FOR ARTICLES AND METHODS FOR USING THE SAME

(71) Applicant: OSSUR HF, Reykjavik (IS)

(72) Inventors: Sindri Pall Sigurdsson, Reykjavik (IS); Bjorn Omarsson, Reykjavik (IS); Stefan Orn Stefansson, Reykjavik (IS)

(73) Assignee: OSSUR HR, Reykjavik (IS)

( * ) Notice: Subject to any disclaimer, the term of this patent is extended or adjusted under 35 U.S.C. 154(b) by 365 days.

This patent is subject to a terminal disclaimer.

(21) Appl. No.: 17/698,538

(22) Filed: Mar. 18, 2022

(65) Prior Publication Data

US 2022/0202604 A1 Jun. 30, 2022

Related U.S. Application Data

(63) Continuation of application No. 16/225,158, filed on Dec. 19, 2018, now Pat. No. 11,304,838, which is a
(Continued)

(51) Int. Cl.
*A61F 5/01* (2006.01)

(52) U.S. Cl.
CPC .............. *A61F 5/0109* (2013.01); *A61F 5/01* (2013.01); *A61F 5/0102* (2013.01);
(Continued)

(58) Field of Classification Search
CPC ........ A61F 5/01; A61F 5/0102; A61F 5/0106; A61F 5/0109; A61F 5/0118;
(Continued)

(56) References Cited

U.S. PATENT DOCUMENTS

| 59,332 A | 10/1866 | White et al. |
| 80,834 A | 8/1868 | Prussia |

(Continued)

FOREIGN PATENT DOCUMENTS

| AT | 127075 B | 2/1932 |
| AT | 244804 B | 1/1966 |

(Continued)

OTHER PUBLICATIONS

"Rollerblade TFS Skate Laces Aero", http://www.inlinewarehouse.com/viewlarge.html?PCODE=TFS, retrieved on Jan. 7, 2010, 1 page.
(Continued)

*Primary Examiner* — Keri J Nelson
(74) *Attorney, Agent, or Firm* — Workman Nydegger

(57) ABSTRACT

A support for an article has a body arranged for length adjustment along a length adjustment axis. A tensioning device is connected to the support and adjustment of the tensioning device shortens or lengthens a length of the support along the length adjustment axis. The body defines at least one opening overlapping at least part of the length adjustment axis such that length adjustment is governed by modification of the size of the at least one opening according to adjustment by the tensioning device.

18 Claims, 12 Drawing Sheets

Related U.S. Application Data continuation of application No. 14/872,277, filed on Oct. 1, 2015, now Pat. No. 10,182,935.

(60) Provisional application No. 62/058,306, filed on Oct. 1, 2014.

(52) U.S. Cl.
CPC .......... *A61F 5/0106* (2013.01); *A61F 5/0123* (2013.01); *A61F 2005/0176* (2013.01); *A61F 2005/0197* (2013.01)

(58) Field of Classification Search
CPC .................... A61F 5/0123; A61F 5/013; A61F 2005/0172; A61F 2005/0176; A61F 2005/0197
See application file for complete search history.

(56) References Cited

U.S. PATENT DOCUMENTS

| | | |
|---|---|---|
| 117,530 A | 8/1871 | Foote |
| 228,946 A | 6/1880 | Schulz |
| 230,759 A | 8/1880 | Drummond |
| 746,563 A | 12/1903 | McMahon |
| 819,993 A | 5/1906 | Haws et al. |
| 908,704 A | 1/1909 | Sprinkle |
| 1,060,422 A | 4/1913 | Bowdish |
| 1,062,511 A | 5/1913 | Short |
| 1,083,775 A | 1/1914 | Thomas |
| 1,090,438 A | 3/1914 | Worth et al. |
| 1,170,472 A | 2/1916 | Barber |
| 1,288,859 A | 12/1918 | Feller et al. |
| 1,390,991 A | 9/1921 | Fotchuk |
| 1,393,188 A | 10/1921 | Whiteman |
| 1,412,486 A | 4/1922 | Paine |
| 1,416,203 A | 5/1922 | Hobson |
| 1,429,657 A | 9/1922 | Trawinski |
| 1,466,673 A | 9/1923 | Solomon et al. |
| 1,469,661 A | 10/1923 | Migita |
| 1,481,903 A | 1/1924 | Hart |
| 1,502,919 A | 7/1924 | Seib |
| 1,530,713 A | 3/1925 | Clark |
| 1,862,047 A | 6/1932 | Boulet et al. |
| 1,995,243 A | 3/1935 | Clarke |
| 2,070,093 A | 2/1937 | Roe |
| 2,088,851 A | 8/1937 | Gantenbein |
| 2,109,751 A | 3/1938 | Matthias et al. |
| 2,124,310 A | 7/1938 | Murr, Jr. |
| 2,316,102 A | 4/1943 | Preston |
| 2,539,026 A | 1/1951 | Mangold |
| 2,611,940 A | 9/1952 | Cairns |
| 2,673,381 A | 3/1954 | Dueker |
| 2,779,110 A | 1/1957 | Howell |
| 2,907,086 A | 10/1959 | Ord |
| 2,991,523 A | 7/1961 | Del Conte |
| 3,035,319 A | 5/1962 | Wolff |
| 3,112,545 A | 12/1963 | Williams |
| 3,163,900 A | 1/1965 | Martin |
| 3,169,325 A | 2/1965 | Fesl |
| 3,193,950 A | 7/1965 | Liou |
| 3,197,155 A | 7/1965 | Chow |
| 3,221,384 A | 12/1965 | Aufenacker |
| 3,276,090 A | 10/1966 | Nigon |
| 3,401,437 A | 9/1968 | Christophersen |
| 3,430,303 A | 3/1969 | Perrin et al. |
| 3,491,465 A | 1/1970 | Martin |
| 3,545,106 A | 12/1970 | Martin |
| 3,618,232 A | 11/1971 | Shnuriwsky |
| 3,668,791 A | 6/1972 | Salzman et al. |
| 3,678,539 A | 7/1972 | Graup |
| 3,703,775 A | 11/1972 | Gatti |
| 3,729,779 A | 5/1973 | Porth |
| 3,738,027 A | 6/1973 | Schoch |
| 3,793,749 A | 2/1974 | Gertsch et al. |
| 3,808,644 A | 5/1974 | Schoch |
| 3,889,664 A | 6/1975 | Heuser et al. |
| 3,926,182 A | 12/1975 | Stabholz |
| 3,934,346 A | 1/1976 | Sasaki et al. |
| 3,975,838 A | 8/1976 | Martin |
| 4,130,949 A | 12/1978 | Seidel |
| 4,142,307 A | 3/1979 | Martin |
| 4,227,322 A | 10/1980 | Annovi |
| 4,261,081 A | 4/1981 | Lott |
| 4,267,622 A | 5/1981 | Burnett-Johnston |
| 4,296,744 A | 10/1981 | Palumbo |
| 4,370,978 A | 2/1983 | Palumbo |
| 4,408,403 A | 10/1983 | Martin |
| 4,423,720 A | 1/1984 | Meier et al. |
| 4,425,912 A | 1/1984 | Harper |
| 4,433,456 A | 2/1984 | Baggio |
| 4,445,505 A | 5/1984 | Labour et al. |
| 4,463,761 A | 8/1984 | Pols et al. |
| 4,480,395 A | 11/1984 | Schoch |
| 4,506,661 A | 3/1985 | Foster |
| 4,507,878 A | 4/1985 | Semouha |
| 4,551,932 A | 11/1985 | Schoch |
| 4,555,830 A | 12/1985 | Petrini et al. |
| 4,574,500 A | 3/1986 | Aldinio et al. |
| 4,607,628 A | 8/1986 | Dashefsky |
| 4,616,524 A | 10/1986 | Bidoia |
| 4,619,057 A | 10/1986 | Sartor et al. |
| 4,619,657 A | 10/1986 | Keates et al. |
| 4,620,378 A | 11/1986 | Sartor |
| 4,631,839 A | 12/1986 | Bonetti et al. |
| 4,631,840 A | 12/1986 | Gamm |
| 4,633,599 A | 1/1987 | Morell et al. |
| 4,654,985 A | 4/1987 | Chalmers |
| 4,660,300 A | 4/1987 | Morell et al. |
| 4,660,302 A | 4/1987 | Arieh et al. |
| 4,680,878 A | 7/1987 | Pozzobon et al. |
| 4,719,670 A | 1/1988 | Kurt |
| 4,719,709 A | 1/1988 | Vaccari |
| 4,719,710 A | 1/1988 | Pozzobon |
| 4,722,477 A | 2/1988 | Floyd |
| 4,741,115 A | 5/1988 | Pozzobon |
| 4,748,726 A | 6/1988 | Schoch |
| 4,760,653 A | 8/1988 | Baggio |
| 4,780,969 A | 11/1988 | White, Jr. |
| 4,787,124 A | 11/1988 | Pozzobon et al. |
| 4,790,081 A | 12/1988 | Benoit et al. |
| 4,796,829 A | 1/1989 | Pozzobon et al. |
| 4,799,297 A | 1/1989 | Baggio et al. |
| 4,802,291 A | 2/1989 | Sartor |
| 4,811,503 A | 3/1989 | Iwama |
| 4,826,098 A | 5/1989 | Pozzobon et al. |
| 4,841,649 A | 6/1989 | Baggio et al. |
| 4,856,207 A | 8/1989 | Datson |
| 4,870,723 A | 10/1989 | Pozzobon et al. |
| 4,870,761 A | 10/1989 | Tracy |
| 4,884,760 A | 12/1989 | Baggio et al. |
| 4,924,605 A | 5/1990 | Spademan |
| 4,937,953 A | 7/1990 | Walkhoff |
| 4,961,544 A | 10/1990 | Bidoia |
| 5,001,817 A | 3/1991 | De Bortoli et al. |
| 5,002,045 A | 3/1991 | Spademan |
| 5,016,327 A | 5/1991 | Klausner |
| 5,024,216 A | 6/1991 | Shiono |
| 5,042,177 A | 8/1991 | Schoch |
| 5,062,225 A | 11/1991 | Gorza |
| 5,065,480 A | 11/1991 | De Bortoli |
| 5,065,481 A | 11/1991 | Walkhoff |
| 5,092,321 A | 3/1992 | Spademan |
| 5,117,567 A | 6/1992 | Berger |
| 5,152,038 A | 10/1992 | Schoch |
| 5,157,813 A | 10/1992 | Carroll |
| 5,158,428 A | 10/1992 | Gessner et al. |
| 5,177,882 A | 1/1993 | Berger |
| 5,181,331 A | 1/1993 | Berger |
| 5,183,036 A | 2/1993 | Spademan |
| 5,184,378 A | 2/1993 | Batra |
| D333,552 S | 3/1993 | Berger et al. |
| 5,249,377 A | 10/1993 | Walkhoff |
| 5,259,094 A | 11/1993 | Zepeda |

(56) References Cited

U.S. PATENT DOCUMENTS

| | | |
|---|---|---|
| 5,277,697 A | 1/1994 | France et al. |
| 5,315,741 A | 5/1994 | Dubberke |
| 5,319,868 A | 6/1994 | Hallenbeck |
| 5,319,869 A | 6/1994 | McDonald et al. |
| 5,325,613 A | 7/1994 | Sussmann |
| 5,327,662 A | 7/1994 | Hallenbeck |
| 5,335,401 A | 8/1994 | Hanson |
| 5,341,583 A | 8/1994 | Hallenbeck |
| 5,345,697 A | 9/1994 | Quellais |
| 5,355,596 A | 10/1994 | Sussmann |
| 5,357,654 A | 10/1994 | Hsing-Chi |
| 5,365,947 A | 11/1994 | Bonutti |
| 5,371,957 A | 12/1994 | Gaudio |
| 5,381,609 A | 1/1995 | Hieblinger |
| 5,392,535 A | 2/1995 | Van Noy et al. |
| 5,411,037 A | 5/1995 | Hess et al. |
| 5,417,646 A | 5/1995 | Gauvry |
| 5,425,161 A | 6/1995 | Schoch |
| 5,425,185 A | 6/1995 | Gansler |
| 5,430,960 A | 7/1995 | Richardson |
| 5,433,648 A | 7/1995 | Frydman |
| 5,437,619 A | 8/1995 | Malewicz et al. |
| 5,463,822 A | 11/1995 | Miller |
| 5,477,593 A | 12/1995 | Leick |
| 5,502,902 A | 4/1996 | Sussmann |
| 5,511,325 A | 4/1996 | Hieblinger |
| 5,535,531 A | 7/1996 | Karabed et al. |
| 5,537,763 A | 7/1996 | Donnadieu et al. |
| 5,554,105 A | 9/1996 | Taylor |
| 5,557,864 A | 9/1996 | Marks |
| 5,566,474 A | 10/1996 | Leick et al. |
| 5,596,820 A | 1/1997 | Edauw et al. |
| 5,599,000 A | 2/1997 | Bennett |
| 5,599,288 A | 2/1997 | Shirley et al. |
| 5,600,874 A | 2/1997 | Jungkind |
| 5,606,778 A | 3/1997 | Jungkind |
| 5,613,943 A | 3/1997 | Palumbo |
| D379,113 S | 5/1997 | McDonald et al. |
| 5,638,588 A | 6/1997 | Jungkind |
| 5,640,785 A | 6/1997 | Egelja |
| 5,647,104 A | 7/1997 | James |
| 5,651,198 A | 7/1997 | Sussmann |
| 5,669,116 A | 9/1997 | Jungkind |
| 5,685,830 A | 11/1997 | Bonutti |
| 5,692,319 A | 12/1997 | Parker et al. |
| 5,718,021 A | 2/1998 | Tatum |
| 5,718,065 A | 2/1998 | Locker |
| 5,720,084 A | 2/1998 | Chen |
| 5,732,483 A | 3/1998 | Cagliari |
| 5,736,696 A | 4/1998 | Del Rosso |
| 5,737,854 A | 4/1998 | Sussmann |
| 5,755,044 A | 5/1998 | Veylupek |
| 5,756,298 A | 5/1998 | Burczak et al. |
| 5,759,167 A | 6/1998 | Shields, Jr. et al. |
| 5,761,777 A | 6/1998 | Leick |
| 5,772,146 A | 6/1998 | Kawamoto et al. |
| 5,784,809 A | 7/1998 | McDonald |
| 5,791,068 A | 8/1998 | Bernier et al. |
| 5,797,864 A | 8/1998 | Taylor |
| 5,807,298 A | 9/1998 | Palumbo |
| 5,819,378 A | 10/1998 | Doyle |
| 5,845,371 A | 12/1998 | Chen |
| 5,848,979 A | 12/1998 | Bonutti et al. |
| 5,865,776 A | 2/1999 | Springs |
| 5,891,061 A | 4/1999 | Kaiser |
| 5,909,946 A | 6/1999 | Okajima |
| 5,934,599 A | 8/1999 | Hammerslag |
| 5,937,542 A | 8/1999 | Bourdeau |
| 5,956,823 A | 9/1999 | Borel |
| 6,052,921 A | 4/2000 | Oreck |
| 6,070,886 A | 6/2000 | Cornelius et al. |
| 6,083,857 A | 7/2000 | Bottger et al. |
| 6,088,936 A | 7/2000 | Bahl |
| 6,102,412 A | 8/2000 | Staffaroni |
| D430,724 S | 9/2000 | Matis et al. |
| 6,119,372 A | 9/2000 | Okajima |
| 6,148,489 A | 11/2000 | Dickie et al. |
| 6,159,248 A | 12/2000 | Gramnas |
| 6,202,953 B1 | 3/2001 | Hammerslag |
| 6,206,932 B1 | 3/2001 | Johnson |
| 6,240,657 B1 | 6/2001 | Weber et al. |
| 6,256,798 B1 | 7/2001 | Egolf et al. |
| 6,267,390 B1 | 7/2001 | Maravetz et al. |
| 6,286,233 B1 | 9/2001 | Gaither |
| 6,287,269 B1 | 9/2001 | Osti et al. |
| 6,289,558 B1 | 9/2001 | Hammerslag |
| 6,311,633 B1 | 11/2001 | Keire |
| 6,393,736 B1 | 5/2002 | Greer, Jr. et al. |
| 6,401,364 B1 | 6/2002 | Burt |
| 6,413,232 B1 | 7/2002 | Townsend et al. |
| 6,416,074 B1 | 7/2002 | Maravetz et al. |
| 6,436,066 B1 | 8/2002 | Lockhart |
| 6,467,195 B2 | 10/2002 | Pierre et al. |
| 6,477,793 B1 | 11/2002 | Pruitt et al. |
| 6,502,577 B1 | 1/2003 | Bonutti |
| 6,503,213 B2 | 1/2003 | Bonutti |
| 6,543,159 B1 | 4/2003 | Carpenter et al. |
| 6,551,264 B1 | 4/2003 | Cawley et al. |
| 6,568,103 B2 | 5/2003 | Durocher |
| 6,606,804 B2 | 8/2003 | Kaneko et al. |
| 6,689,080 B2 | 2/2004 | Castillo |
| 6,694,643 B1 | 2/2004 | Hsu |
| 6,708,376 B1 | 3/2004 | Landry |
| 6,711,787 B2 | 3/2004 | Jungkind et al. |
| 6,735,829 B2 | 5/2004 | Hsu |
| 6,757,991 B2 | 7/2004 | Sussmann |
| 6,769,155 B2 | 8/2004 | Hess et al. |
| 6,770,047 B2 | 8/2004 | Bonutti |
| 6,775,928 B2 | 8/2004 | Grande et al. |
| 6,792,702 B2 | 9/2004 | Borsoi et al. |
| 6,802,439 B2 | 10/2004 | Azam et al. |
| 6,823,610 B1 | 11/2004 | Ashley |
| 6,827,653 B2 | 12/2004 | Be |
| 6,877,256 B2 | 4/2005 | Martin et al. |
| 6,921,377 B2 | 7/2005 | Bonutti |
| 6,922,917 B2 | 8/2005 | Kerns et al. |
| 6,938,913 B2 | 9/2005 | Elkington |
| 6,945,543 B2 | 9/2005 | De Bortoli et al. |
| 6,976,972 B2 | 12/2005 | Bradshaw |
| 6,993,859 B2 | 2/2006 | Martin et al. |
| 7,004,919 B2 | 2/2006 | Gaylord et al. |
| 7,011,641 B1 | 3/2006 | Detoro et al. |
| D519,637 S | 4/2006 | Nordt et al. |
| D520,141 S | 5/2006 | Nordt et al. |
| D521,226 S | 5/2006 | Douglas et al. |
| D521,644 S | 5/2006 | Nordt et al. |
| 7,060,045 B2 | 6/2006 | Mason et al. |
| 7,076,843 B2 | 7/2006 | Sakabayashi |
| 7,082,652 B2 | 8/2006 | St-Louis et al. |
| 7,082,701 B2 | 8/2006 | Dalgaard et al. |
| 7,083,586 B2 | 8/2006 | Simmons et al. |
| 7,096,559 B2 | 8/2006 | Johnson |
| 7,128,724 B2 | 10/2006 | Marsh |
| 7,134,224 B2 | 11/2006 | Elkington et al. |
| 7,198,610 B2 | 4/2007 | Ingimundarson et al. |
| 7,207,126 B2 | 4/2007 | Gantier |
| 7,235,059 B2 | 6/2007 | Mason et al. |
| 7,266,911 B2 | 9/2007 | Holzer et al. |
| 7,281,341 B2 | 10/2007 | Reagan et al. |
| 7,293,373 B2 | 11/2007 | Reagan et al. |
| 7,306,573 B2 | 12/2007 | Bonutti |
| 7,331,126 B2 | 2/2008 | Johnson |
| 7,343,701 B2 | 3/2008 | Pare et al. |
| 7,360,282 B2 | 4/2008 | Borsoi |
| 7,367,522 B2 | 5/2008 | Chen |
| 7,386,947 B2 | 6/2008 | Martin et al. |
| 7,392,602 B2 | 7/2008 | Reagan et al. |
| 7,401,423 B2 | 7/2008 | Reagan et al. |
| 7,402,147 B1 | 7/2008 | Allen |
| 7,404,804 B2 | 7/2008 | Bonutti |
| 7,416,565 B1 | 8/2008 | Al-Turaikl |
| 7,438,698 B2 | 10/2008 | Daiju |
| 7,490,458 B2 | 2/2009 | Ford |
| 7,513,018 B2 | 4/2009 | Koenig et al. |

(56) References Cited

U.S. PATENT DOCUMENTS

| | | |
|---|---|---|
| 7,568,298 B2 | 8/2009 | Kerns |
| 7,584,528 B2 | 9/2009 | Hu |
| 7,591,050 B2 | 9/2009 | Hammerslag |
| 7,597,675 B2 | 10/2009 | Ingimundarson et al. |
| 7,600,660 B2 | 10/2009 | Kasper et al. |
| 7,617,573 B2 | 11/2009 | Chen |
| 7,618,386 B2 | 11/2009 | Nordt, III et al. |
| 7,618,389 B2 | 11/2009 | Nordt, III et al. |
| 7,624,517 B2 | 12/2009 | Smith |
| 7,648,404 B1 | 1/2010 | Martin |
| 7,650,705 B2 | 1/2010 | Donnadieu et al. |
| 7,662,122 B2 | 2/2010 | Sterling |
| 7,670,306 B2 | 3/2010 | Nordt, III et al. |
| 7,694,354 B2 | 4/2010 | Philpott et al. |
| 7,699,797 B2 | 4/2010 | Nordt, III et al. |
| 7,704,219 B2 | 4/2010 | Nordt, III et al. |
| 7,713,225 B2 | 5/2010 | Ingimundarson et al. |
| 7,749,181 B2 | 7/2010 | Simmons et al. |
| 7,757,412 B2 | 7/2010 | Farys |
| 7,774,956 B2 | 8/2010 | Dua et al. |
| 7,794,418 B2 | 9/2010 | Ingimundarson et al. |
| 7,806,842 B2 | 10/2010 | Stevenson et al. |
| 7,819,830 B2 | 10/2010 | Sindel et al. |
| 7,841,106 B2 | 11/2010 | Farys |
| 7,857,776 B2 | 12/2010 | Frisbie |
| 7,862,528 B2 | 1/2011 | Scott |
| 7,862,621 B2 | 1/2011 | Kloos et al. |
| 7,867,183 B2 | 1/2011 | Kazmierczak et al. |
| 7,871,334 B2 | 1/2011 | Young et al. |
| 7,877,845 B2 | 2/2011 | Signori |
| 7,878,998 B2 | 2/2011 | Nordt, III et al. |
| 7,887,500 B2 | 2/2011 | Nordt, III et al. |
| 7,896,827 B2 | 3/2011 | Ingimundarson et al. |
| 7,908,769 B2 | 3/2011 | Pellegrini |
| 7,922,680 B2 | 4/2011 | Nordt, III et al. |
| 7,950,112 B2 | 5/2011 | Hammerslag et al. |
| 7,954,204 B2 | 6/2011 | Hammerslag et al. |
| 7,959,590 B2 | 6/2011 | Scott |
| 7,963,049 B2 | 6/2011 | Messmer |
| 7,992,261 B2 | 8/2011 | Hammerslag et al. |
| 7,993,296 B2 | 8/2011 | Nordt, III et al. |
| 8,002,724 B2 | 8/2011 | Hu et al. |
| D646,790 S | 10/2011 | Castillo et al. |
| 8,038,635 B2 | 10/2011 | Dellanno |
| 8,038,637 B2 | 10/2011 | Bonutti |
| 8,056,150 B2 | 11/2011 | Stokes et al. |
| 8,074,379 B2 | 12/2011 | Robinson, Jr. et al. |
| 8,091,182 B2 | 1/2012 | Hammerslag et al. |
| 8,109,015 B2 | 2/2012 | Signori |
| D663,850 S | 7/2012 | Joseph |
| D663,851 S | 7/2012 | Joseph |
| 8,215,033 B2 | 7/2012 | Carboy et al. |
| 8,231,074 B2 | 7/2012 | Hu et al. |
| D665,088 S | 8/2012 | Joseph |
| 8,235,321 B2 | 8/2012 | Chen |
| 8,245,371 B2 | 8/2012 | Chen |
| 8,266,827 B2 | 9/2012 | Dojan et al. |
| 8,277,401 B2 | 10/2012 | Hammerslag et al. |
| 8,302,329 B2 | 11/2012 | Hurd et al. |
| 8,303,527 B2 | 11/2012 | Joseph |
| 8,308,098 B2 | 11/2012 | Chen |
| 8,353,087 B2 | 1/2013 | Chen |
| 8,434,200 B2 | 5/2013 | Chen |
| 8,713,820 B2 | 5/2014 | Kerns et al. |
| 9,125,730 B2 | 9/2015 | Ingimundarson et al. |
| 10,182,935 B2 | 1/2019 | Sigurdsson et al. |
| 11,304,838 B2 * | 4/2022 | Sigurdsson ........... A61F 5/0109 |
| 2002/0050076 A1 | 5/2002 | Borsoi et al. |
| 2002/0062579 A1 | 5/2002 | Caeran |
| 2002/0095750 A1 | 7/2002 | Hammerslag |
| 2002/0129518 A1 | 9/2002 | Borsoi et al. |
| 2002/0133108 A1 | 9/2002 | Jagodzinski |
| 2002/0148142 A1 | 10/2002 | Dorei et al. |
| 2002/0166260 A1 | 11/2002 | Borsoi |
| 2002/0178548 A1 | 12/2002 | Freed |
| 2003/0079376 A1 | 5/2003 | Oorei et al. |
| 2003/0093882 A1 | 5/2003 | Gorza et al. |
| 2003/0177662 A1 | 9/2003 | Elkington et al. |
| 2003/0204156 A1 | 10/2003 | Nelson et al. |
| 2003/0204938 A1 | 11/2003 | Hammerslag |
| 2004/0054307 A1 | 3/2004 | Mason et al. |
| 2004/0176715 A1 | 9/2004 | Nelson |
| 2005/0004499 A1 | 1/2005 | Bauerfeind et al. |
| 2005/0054962 A1 | 3/2005 | Bradshaw |
| 2005/0060912 A1 | 3/2005 | Holzer et al. |
| 2005/0081339 A1 | 4/2005 | Sakabayashi |
| 2005/0081403 A1 | 4/2005 | Mathieu |
| 2005/0087115 A1 | 4/2005 | Martin |
| 2005/0098673 A1 | 5/2005 | Huang |
| 2005/0102861 A1 | 5/2005 | Martin |
| 2005/0126043 A1 | 6/2005 | Reagan et al. |
| 2005/0160627 A1 | 7/2005 | Dalgaard et al. |
| 2005/0198866 A1 | 9/2005 | Wiper et al. |
| 2005/0247813 A1 | 11/2005 | Kovacevich et al. |
| 2005/0273025 A1 | 12/2005 | Houser |
| 2005/0284003 A1 | 12/2005 | Dalgaard et al. |
| 2006/0015980 A1 | 1/2006 | Nordt, III et al. |
| 2006/0015988 A1 | 1/2006 | Philpott et al. |
| 2006/0020237 A1 | 1/2006 | Nordt, III et al. |
| 2006/0026732 A1 | 2/2006 | Nordt, III et al. |
| 2006/0026733 A1 | 2/2006 | Nordt, III et al. |
| 2006/0026736 A1 | 2/2006 | Nordt, III et al. |
| 2006/0030802 A1 | 2/2006 | Nordt, III et al. |
| 2006/0030803 A1 | 2/2006 | Nordt, III et al. |
| 2006/0030804 A1 | 2/2006 | Nordt, III et al. |
| 2006/0030805 A1 | 2/2006 | Nordt, III et al. |
| 2006/0030806 A1 | 2/2006 | Nordt, III et al. |
| 2006/0070164 A1 | 4/2006 | Nordt, III et al. |
| 2006/0070165 A1 | 4/2006 | Nordt, III et al. |
| 2006/0156517 A1 | 7/2006 | Hammerslag et al. |
| 2006/0174516 A1 | 8/2006 | Peruzzo |
| 2006/0179685 A1 | 8/2006 | Borel et al. |
| 2006/0185193 A1 | 8/2006 | Pellegrini |
| 2006/0185357 A1 | 8/2006 | Kovacevich et al. |
| 2006/0202077 A1 | 9/2006 | Kovacevich et al. |
| 2006/0202078 A1 | 9/2006 | Kovacevich et al. |
| 2007/0039085 A1 | 2/2007 | Kovacevich et al. |
| 2007/0063459 A1 | 3/2007 | Kavarsky |
| 2007/0068040 A1 | 3/2007 | Farys |
| 2007/0084956 A1 | 4/2007 | Chen |
| 2007/0113524 A1 | 5/2007 | Lander |
| 2007/0128959 A1 | 6/2007 | Cooke |
| 2007/0169378 A1 | 7/2007 | Sodeberg et al. |
| 2008/0016717 A1 | 1/2008 | Ruban |
| 2008/0034459 A1 | 2/2008 | Nordt, III et al. |
| 2008/0039757 A1 | 2/2008 | Nordt, III et al. |
| 2008/0039764 A1 | 2/2008 | Nordt, III et al. |
| 2008/0039765 A1 | 2/2008 | Nordt, III et al. |
| 2008/0039767 A1 | 2/2008 | Nordt, III et al. |
| 2008/0060167 A1 | 3/2008 | Hammerslag et al. |
| 2008/0060168 A1 | 3/2008 | Hammerslag et al. |
| 2008/0066272 A1 | 3/2008 | Hammerslag et al. |
| 2008/0066345 A1 | 3/2008 | Hammerslag et al. |
| 2008/0066346 A1 | 3/2008 | Hammerslag et al. |
| 2008/0083135 A1 | 4/2008 | Hammerslag et al. |
| 2008/0091132 A1 | 4/2008 | Bonutti |
| 2008/0139985 A1 | 6/2008 | Gilmour |
| 2008/0172848 A1 | 7/2008 | Chen |
| 2008/0319362 A1 | 12/2008 | Joseph |
| 2009/0030353 A1 | 1/2009 | Bonutti et al. |
| 2009/0054819 A1 | 2/2009 | Einarsson |
| 2009/0071041 A1 | 3/2009 | Hooper |
| 2009/0090026 A1 | 4/2009 | Mosher |
| 2009/0090029 A1 | 4/2009 | Kishino |
| 2009/0131844 A1 | 5/2009 | Dean et al. |
| 2009/0172928 A1 | 7/2009 | Messmer et al. |
| 2009/0184189 A1 | 7/2009 | Soderberg et al. |
| 2009/0277043 A1 | 11/2009 | Graser et al. |
| 2009/0287128 A1 | 11/2009 | Ingimundarson et al. |
| 2010/0064547 A1 | 3/2010 | Kaplan et al. |
| 2010/0101061 A1 | 4/2010 | Ha |
| 2010/0139057 A1 | 6/2010 | Soderberg et al. |
| 2010/0154254 A1 | 6/2010 | Fletcher |
| 2010/0175163 A1 | 7/2010 | Litke |

(56) References Cited

U.S. PATENT DOCUMENTS

| | | | |
|---|---|---|---|
| 2010/0251524 A1 | 10/2010 | Chen | |
| 2010/0268139 A1 | 10/2010 | Garth | |
| 2010/0274364 A1 | 10/2010 | Pacanowsky et al. | |
| 2010/0299959 A1 | 12/2010 | Hammerslag et al. | |
| 2010/0319216 A1 | 12/2010 | Grenzke et al. | |
| 2011/0000173 A1 | 1/2011 | Lander | |
| 2011/0046528 A1 | 2/2011 | Stevenson et al. | |
| 2011/0071647 A1 | 3/2011 | Mahon | |
| 2011/0082402 A1 | 4/2011 | Oddou et al. | |
| 2011/0098618 A1 | 4/2011 | Fleming | |
| 2011/0137220 A1 | 6/2011 | Vollbrecht et al. | |
| 2011/0144554 A1 | 6/2011 | Weaver, II et al. | |
| 2011/0167543 A1 | 7/2011 | Kovacevich et al. | |
| 2011/0178448 A1 | 7/2011 | Einarsson | |
| 2011/0184326 A1 | 7/2011 | Ingimundarson et al. | |
| 2011/0191992 A1 | 8/2011 | Chen | |
| 2011/0197362 A1 | 8/2011 | Chella et al. | |
| 2011/0258876 A1 | 10/2011 | Baker et al. | |
| 2011/0266384 A1 | 11/2011 | Goodman et al. | |
| 2012/0000091 A1 | 1/2012 | Cotterman et al. | |
| 2012/0004587 A1 | 1/2012 | Nickel et al. | |
| 2012/0005995 A1 | 1/2012 | Emery | |
| 2012/0010547 A1 | 1/2012 | Hinds | |
| 2012/0023717 A1 | 2/2012 | Chen | |
| 2012/0029404 A1 | 2/2012 | Weaver, II et al. | |
| 2012/0101417 A1 | 4/2012 | Joseph | |
| 2012/0102783 A1 | 5/2012 | Swigart et al. | |
| 2012/0157902 A1 | 6/2012 | Castillo et al. | |
| 2012/0204381 A1 | 8/2012 | Ingimundarson et al. | |
| 2012/0228419 A1 | 9/2012 | Chen | |
| 2012/0246974 A1 | 10/2012 | Hammerslag et al. | |
| 2013/0012856 A1 | 1/2013 | Hammerslag et al. | |
| 2013/0014359 A1 | 1/2013 | Chen | |
| 2013/0025100 A1 | 1/2013 | Ha | |
| 2013/0091667 A1 | 4/2013 | Zerfas et al. | |
| 2013/0092780 A1 | 4/2013 | Soderberg et al. | |
| 2013/0172797 A1 | 7/2013 | Merkley et al. | |
| 2013/0184628 A1 | 7/2013 | Ingimundarson et al. | |
| 2013/0245522 A1 | 9/2013 | Modglin | |
| 2013/0317788 A1 | 11/2013 | Summit et al. | |
| 2013/0340283 A1 | 12/2013 | Bell et al. | |
| 2014/0123440 A1 | 5/2014 | Capra et al. | |
| 2014/0123449 A1 | 5/2014 | Soderberg et al. | |
| 2015/0150705 A1 | 6/2015 | Capra et al. | |
| 2015/0190262 A1 | 7/2015 | Capra et al. | |

FOREIGN PATENT DOCUMENTS

| | | |
|---|---|---|
| AT | 361 808 B | 4/1981 |
| CA | 2 112 789 A1 | 8/1994 |
| CA | 2 114 387 A1 | 8/1994 |
| CH | 41765 A | 11/1908 |
| CH | 111341 A | 11/1925 |
| CH | 199766 A | 9/1938 |
| CH | 204834 A | 5/1939 |
| CH | 471553 A | 4/1969 |
| CH | 523669 A | 6/1972 |
| CH | 537164 A | 5/1973 |
| CH | 562015 A5 | 5/1975 |
| CH | 577 282 A5 | 7/1976 |
| CH | 612 076 A5 | 7/1979 |
| CH | 624 001 A5 | 7/1981 |
| DE | 555 211 C | 7/1932 |
| DE | 641 976 C | 2/1937 |
| DE | 1661668 U | 8/1953 |
| DE | 7043154 U | 3/1971 |
| DE | 1 785 220 A1 | 5/1971 |
| DE | 2 062 795 A1 | 6/1972 |
| DE | 2 341 658 A1 | 3/1974 |
| DE | 24 14 439 A1 | 10/1975 |
| DE | 29 00 077 A1 | 7/1980 |
| DE | 29 14 280 A1 | 10/1980 |
| DE | 31 01 952 A1 | 9/1982 |
| DE | 36 26 837 A1 | 2/1988 |
| DE | 38 13 470 A1 | 11/1989 |
| DE | 38 22 113 A1 | 1/1990 |
| DE | 43 02 401 A1 | 8/1994 |
| DE | 94 13 147 U1 | 10/1994 |
| DE | 93 15 776.2 U1 | 2/1995 |
| DE | 295 03 552.8 U1 | 4/1995 |
| DE | 196 24 553 A1 | 1/1998 |
| DE | 199 45 045 A1 | 3/2001 |
| DE | 201 16 755 U1 | 1/2002 |
| DE | 100 57 286 A1 | 5/2002 |
| EP | 0 123 050 A1 | 10/1984 |
| EP | 0 081 042 B1 | 12/1984 |
| EP | 0 056 953 B1 | 11/1985 |
| EP | 0 201 051 A1 | 11/1986 |
| EP | 0 099 504 B1 | 1/1987 |
| EP | 0 155 596 B1 | 1/1988 |
| EP | 0 393 380 B1 | 9/1992 |
| EP | 0 255 869 B1 | 1/1993 |
| EP | 0 474 708 B1 | 9/1993 |
| EP | 0 589 233 A1 | 3/1994 |
| EP | 0 614 624 A1 | 9/1994 |
| EP | 0 614 625 A1 | 9/1994 |
| EP | 0 589 232 B1 | 11/1995 |
| EP | 0 679 346 A1 | 11/1995 |
| EP | 0 717 942 A1 | 6/1996 |
| EP | 0 734 662 A1 | 10/1996 |
| EP | 0 693 260 B1 | 9/1998 |
| EP | 0 651 954 B1 | 2/1999 |
| EP | 0 858 621 B1 | 3/1999 |
| EP | 0 858 619 B1 | 4/1999 |
| EP | 0 937 467 A1 | 8/1999 |
| EP | 0 941 722 A1 | 9/1999 |
| EP | 1 219 195 A1 | 7/2002 |
| EP | 1 236 412 A1 | 9/2002 |
| EP | 0 848 917 B2 | 3/2004 |
| EP | 1 163 860 B1 | 7/2005 |
| EP | 0 923 965 B1 | 11/2005 |
| EP | 2 359 708 A1 | 8/2011 |
| FR | 1 349 832 A | 1/1964 |
| FR | 1 374 110 A | 10/1964 |
| FR | 1 404 799 A | 7/1965 |
| FR | 2 019 991 A1 | 7/1970 |
| FR | 2 108 428 A5 | 5/1972 |
| FR | 2 108 429 A5 | 5/1972 |
| FR | 2 173 451 A5 | 10/1973 |
| FR | 2 175 684 A1 | 10/1973 |
| FR | 2 177 294 A6 | 11/1973 |
| FR | 2 399 811 A1 | 3/1979 |
| FR | 2 565 795 A1 | 12/1985 |
| FR | 2 598 292 A1 | 11/1987 |
| FR | 2 726 440 A1 | 5/1996 |
| FR | 2 770 379 A1 | 5/1999 |
| FR | 2 814 919 A1 | 4/2002 |
| GB | 216 400 A | 5/1924 |
| GB | 2 449 722 B | 5/2010 |
| IT | 1220811 B | 6/1990 |
| IT | 2003 000197 A | 10/2003 |
| JP | S51-2776 Y1 | 1/1976 |
| JP | S51-121375 A | 10/1976 |
| JP | S51-131978 U | 10/1976 |
| JP | S53-124987 A | 10/1978 |
| JP | S54-108125 A | 8/1979 |
| JP | S62-57346 U | 4/1987 |
| JP | S62-84906 U | 5/1987 |
| JP | S63-80736 U | 5/1988 |
| JP | 7-208 A | 6/1995 |
| JP | 3030988 U | 11/1996 |
| JP | H08-308608 A | 11/1996 |
| JP | 3031760 U | 12/1996 |
| JP | H10-199366 A | 7/1998 |
| JP | 2001-197905 A | 7/2001 |
| JP | 2004-016732 A | 1/2004 |
| JP | 2004-041666 A | 2/2004 |
| JP | 4928618 B2 | 5/2012 |
| KR | 20-0367882 Y1 | 11/2004 |
| KR | 20-0400568 Y1 | 11/2005 |
| KR | 10-0598627 B1 | 7/2006 |
| KR | 10-0953398 B1 | 4/2010 |
| KR | 10-1028468 B1 | 4/2011 |
| WO | 94/27456 A1 | 12/1994 |

(56) References Cited

FOREIGN PATENT DOCUMENTS

| WO | 95/03720 A2 | 2/1995 |
|---|---|---|
| WO | 95/11602 A1 | 5/1995 |
| WO | 97/03581 A1 | 2/1997 |
| WO | 98/37782 A1 | 9/1998 |
| WO | 99/09850 A1 | 3/1999 |
| WO | 99/15043 A1 | 4/1999 |
| WO | 99/43231 A1 | 9/1999 |
| WO | 00/53045 A1 | 9/2000 |
| WO | 00/76337 A1 | 12/2000 |
| WO | 01/08525 A1 | 2/2001 |
| WO | 02/051511 A1 | 7/2002 |
| WO | 2004/093569 A1 | 11/2004 |
| WO | 2004/110197 A2 | 12/2004 |
| WO | 2007/016983 A1 | 2/2007 |
| WO | 2008/015214 A1 | 2/2008 |
| WO | 2013138214 A1 | 9/2013 |
| WO | 2015/035885 A1 | 3/2015 |

OTHER PUBLICATIONS

"Rollerblade TFS Skate Laces Micro", http://www.inlinewarehouse.com/viewlarge.html?PCODE=MILC, retrieved on Jan. 7, 2010, 1 page.
International Search Report from International Application No. PCT/US2013/030711, Jun. 12, 2013.
International Search Report from PCT Application No. PCT/US2015/053401, Oct. 1, 2015.

\* cited by examiner

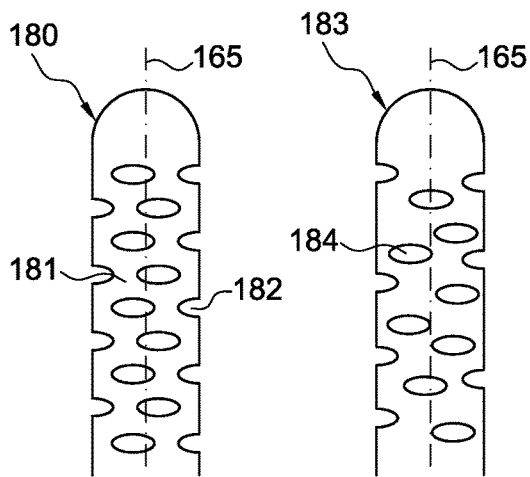
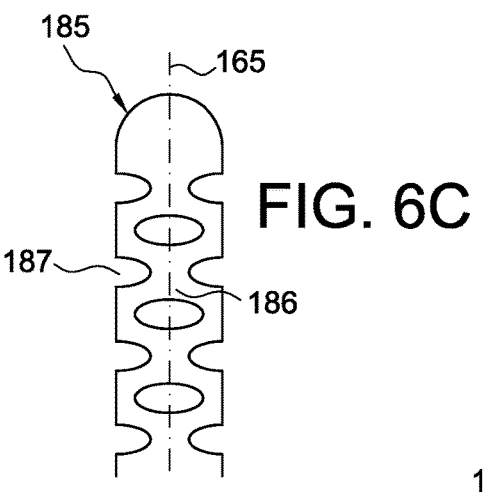
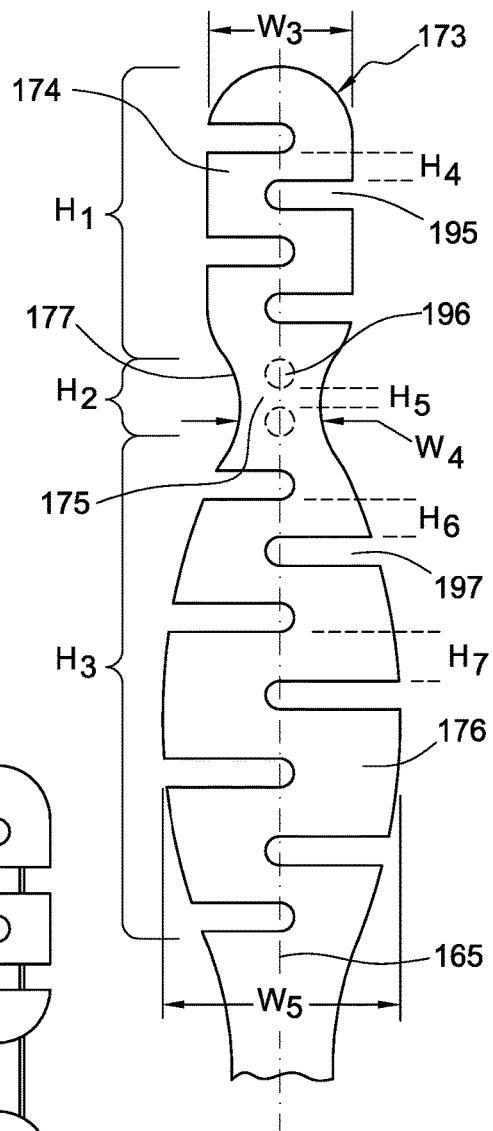
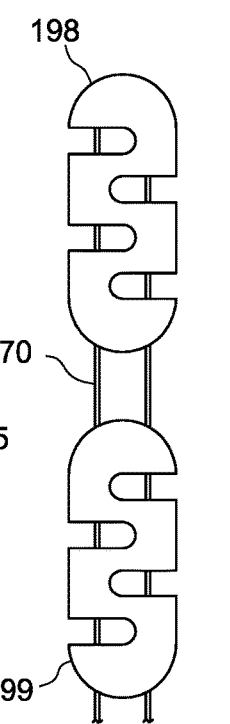
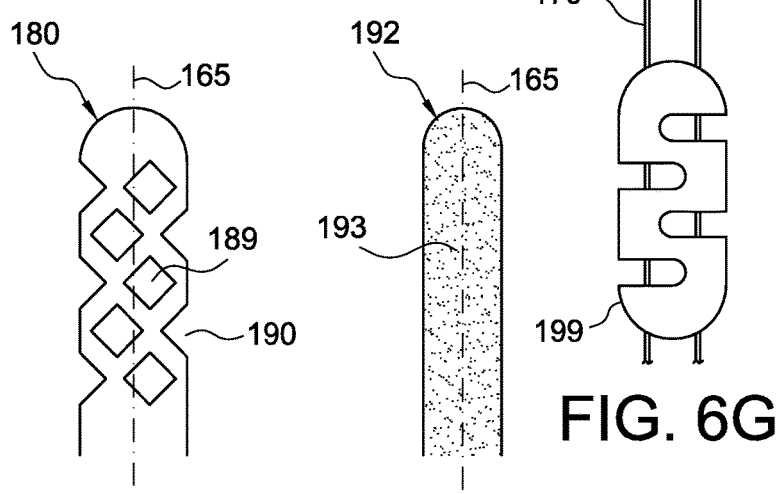
FIG. 6A  FIG. 6B  FIG. 6C  FIG. 6D  FIG. 6E  FIG. 6F  FIG. 6G

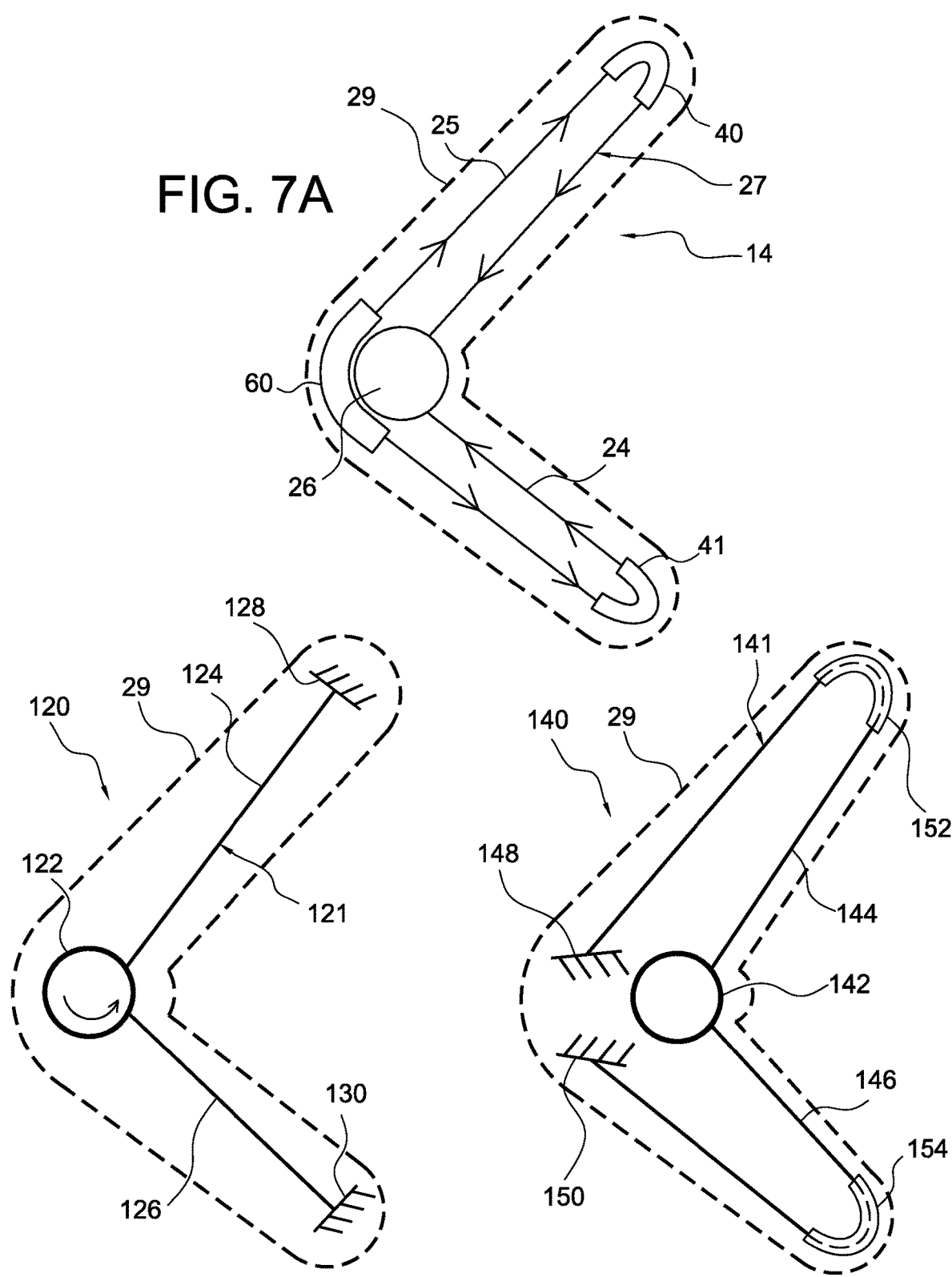

SUPPORT FOR ARTICLES AND METHODS FOR USING THE SAME

FIELD OF THE DISCLOSURE

The disclosure relates to a support for articles and methods for using the same. In a preferred embodiment, a support is arranged to provide incremental stabilization and compression to a patella and may be used alone or in combination with an orthopedic device.

BACKGROUND

Supports and straps are used in various articles for supporting, placement or closure about a body part. Straps are conventionally used for being tensioned or used to increase the fit or comfort of the article. The straps may be combined with supports for stabilizing or compressing against a body part. Often, however, supports are statically attached to an article and straps are separately positioned or spaced from the article.

While supports and straps may be used in different articles, they are predominately found in orthopedic devices. In an example, there are numerous orthopedic devices such as braces that provide support around a patella of a user. Many of these braces use a stationary or static support that provides support about the patella of the user.

Some of the known braces include a front central opening that allow for the wearer's patella or kneecap to project therethrough. The front central opening relieves pressure otherwise exerted on the patella, particularly when the knee is bent or in flexion. These braces may include a pad or support located about the front central opening to provide a restraining force to the patella and additional support for preventing lateral or medial displacement of the patella in the femoral groove.

Despite known solutions, many braces fail to maintain the support in a proper position on the patella so the opening or support can prevent patella displacement, in part due to their static arrangement; they are not arranged to accommodate movement or flexion of the knee.

Alternatively, another example of a brace has a strap and a patella support attached to the strap for applying patellar support. One end of the strap has the patella support fixed near the patella of a user and a second end secures to a connection point along a lateral or medial side of the brace. As the strap is tensioned, the support applies pressure about the patella. The support itself, however, does not change in shape according to exertion of tension in the straps; rather they are merely compressed against the knee.

Many known devices fail to maintain the support in a proper position on the patella so the opening or support can prevent patella displacement. Therefore, there is a need for a knee brace that at least provides means for stabilizing and supporting the patella.

A large group of people suffer from patellofemoral osteoarthritis (OA); either stand-alone patellofemoral OA or, in combination with medial or lateral side OA. There are few if any commercial patellofemoral OA solutions on the market.

A purpose of a patellofemoral OA brace is to relieve knee pain caused by OA in the patellofemoral joint. An unloading type knee brace provides a solution for people with medial or lateral side knee OA, such as one described in U.S. Pat. No. 7,198,610, granted Apr. 3, 2007, and incorporated herein by reference. There exists no solution that targets individuals suffering from stand-alone patellofemoral pain and in combination with medial side OA.

SUMMARY

The combination of the patellofemoral (PF) joint and OA is a significant problem for the patient as is OA in the tibiofemoral (TF) joint. The solutions described herein are aimed for the sufferer of combined TF/PF OA, as the pain may originate from either or both joints. For the combined TF/PF condition, treating the TF joint alone may not be sufficient. Solutions are also described to treating isolated PF OA or PF instability or deficiencies.

Various solutions relied upon to treat PF OA may employ a compressive sleeve with inelastic or elastic parts, a compressive padding and/or various strap arrangements. Particularly, the compressive padding may include an arcuate pad or strap system with and without variable tensioning, such as in dial tensioning.

In one variation, the solution relies on moving the patella medially and securing it in position by a variety of techniques. Patellar maltracking usually means that the patella is positioned too far on the lateral side. Because of PF problems, the patella is almost always pulled medially.

Embodiments of the patella device are adjustable, reliable and durable, and may mimic various taping techniques. Realignment of the patella places it more properly in the trochlea groove. In the aligned position, the PF joint's articulation surface is increased and the increased surface of articulation means the joint loads are more evenly distributed and high local forces are prevented.

A pad or support may be used or added to the support to contribute to the sideway force. The support creates extra surface area and holds a side of the patella, either alone or in combination with a strap, to focus and direct the force. The support is preferably adjustable and allows adjustment of the direction of the force providing the user the opportunity to adjust the direction of the applied force according to the user's condition. The point of friction in the patellofemoral joint can vary between persons and the support can be positioned around the area of the pain.

In an embodiment, a strap may be attached to a support that sits on top of the sleeve. By attaching the strap to the support, a stable anchoring point is created. There may be a benefit in attaching the strap to the medial side of the sleeve or attaching it to the lateral side of the sleeve and placing the attachment point on the medial side. Attaching the strap to the sleeve may improve comfort and enables the user to use the sleeve independent of an unloader brace.

Embodiments may employ a C-shaped strap or support, and may include a tensioning device that adjusts the C-strap or support. This embodiment rests on the concept of adjustably unloading the patella by tensioning which pushes the knee into the hinge creating an unloading force.

Variations may be arranged to increase forces on the patella as the knee flexes such that as the knee flexes, the force on the patella increases medially. The varations may be adjustable with a dial tensioning system whereby the support includes at least one adjustable anchor point. This arrangement provides the user the possibility to position the support as needed and apply a suitable amount of force.

In an embodiment, the patella device includes a sleeve defining first and second sides divided by a medial-lateral plane, and a central portion defined along an anterior side of an anterior-posterior plane. A support has a body defining a first end anchored to the first side of the sleeve and a middle portion anchored to the second side of the sleeve. The support is located proximate the central portion which may define an opening. The support may define at least one opening formed along the length of the support and extends from a periphery into a width of the support. The at least one opening may be defined by a first set of openings formed along a first periphery and a second set of openings is formed along a second periphery. The first and second openings alternate relative to one another along a length of the support.

A tensioning device is coupled to the support and adjusts the length of the support by opening or compressing the openings. The support may operate in the manner of an accordion by the openings to conform to the user's anatomy and facilitate force generation over the patella. The tensioning enables selective tensioning of the support.

According to an embodiment, the body defines a length adjustment axis, which may be located generally along a midline of the body. The length adjustment axis depends upon the contour of the body such that the body may bend and the length adjustment axis follows the bend. At least one of the openings overlaps at least part of the length adjustment axis such that length adjustment is governed by modification of the size of the at least one opening according to adjustment by the tensioning device.

In an embodiment, the body defines at least one opening overlapping at least part of the length adjustment axis such that length adjustment is governed by modification of the size of the at least one opening according to adjustment by the tensioning device. The at least one opening may be formed along the length of the support and extend from a periphery into a width of the support. The at least one opening extends past the length adjustment axis of the support from the periphery.

According to an example, the at least one opening may define first and second ends with the first end extending past the length adjustment axis short of a first periphery and the second end defined by opposed side portions arranged to clamp against one another depending on the length of the support. The first and second openings alternating relative to one another along a length of the support.

At least one cable may be linked to the tensioning device and cooperates with the support to adjust the length thereof by actuation of the tensioning device. The at least one cable may extend through a thickness of the body of the support from the first portion to the second portion such that actuation of the tensioning device adjusts the length of the at least one cable to adjust the length of the support. The at least one cable may intersect or pass through one of the openings in the body of the support.

According to a variation, the at least one cable includes first and second cable segments linked to the tensioning device and extending to the first and second portions, respectively. The first and second cable segments are individually attached to the tensioning device and operated independently from one another by each having an end opposite from a portion engaging the tensioning device. The first and second cable segments may form a loop with the tensioning device and are regulated simultaneously and dependently with one another.

The support may be arranged in a variety of geometries, whether shape profile, height, width, thickness or length. The opening can be modified likewise according intended usage of the support.

A method for adjusting a length of the support includes adjusting tension in the at least one cable by regulating the tensioning device and causing geometry of the at least one opening to modify according to tension in the cable. Depending on usage and application of the support, additional steps may include anchoring first and second ends of the support to first and second locations, the length of the support adjusting along the length adjustment axis according to regulation of the tensioning device; providing at least one peripheral opening along a periphery of the support; and contouring a shape of the support according to regulation of the tensioning device by modifying a geometry of the peripheral opening as a result in adjustment of tension in the at least one cable.

According to an embodiment in the form of an orthopedic device, the support tracks the patella and provides support. The support and straps associated with the sleeve creates a medial/lateral force that tracks the patella in a desired direction (lateral or medial). The support may be used along or in combination with an OA brace.

The support provides dynamic tracking of the patella by its ability to adapt in shape as the support is tensioned. The support combines function of both a strap and a support because the support itself is tensioned and adapted to adjust in geometry according to the tensioning of the support. The support may have compressible features, such as a body forming part of the support as constructed from a porous or compressible material such as foam.

The support may be adapted as a strap in part due to its ability to resize according to tension in the support. An advantage of the strap is that it may cover greater surface area to better distribute tension over the object by which it is secured, as in a body part. In another use, the support may be arranged to provide increased or decreased rigidity because of tensioning the support, in part by adjusting rigidity of a support body or geometry of the support body.

The support is not limited to use in a PF support, but may be used in articles and applications requiring stabilization, closure, compression, rigidity and other expedients.

DESCRIPTION OF THE DRAWINGS

The support is described referring to the accompanying drawings, which show preferred embodiments according to the device described. The device and method as disclosed in the accompanying drawings are illustrated for example only. The elements and combinations of elements described below and illustrated in the drawings can be arranged and organized differently to result in embodiments still within the spirit and scope of the device described.

FIGS. 6A-6E are schematic views showing alternative openings in a support or strap.

FIG. 6F is a schematic view showing a variation of a support or strap.

FIG. 6G is a schematic view showing another variation of a support or strap.

FIG. 7A is a schematic view showing a cable system in the support of FIG. 1.

FIG. 7B is a schematic view showing another cable system.

FIG. 7C is a schematic view showing another cable system.

DETAILED DESCRIPTION OF VARIOUS EMBODIMENTS

Figure 1:
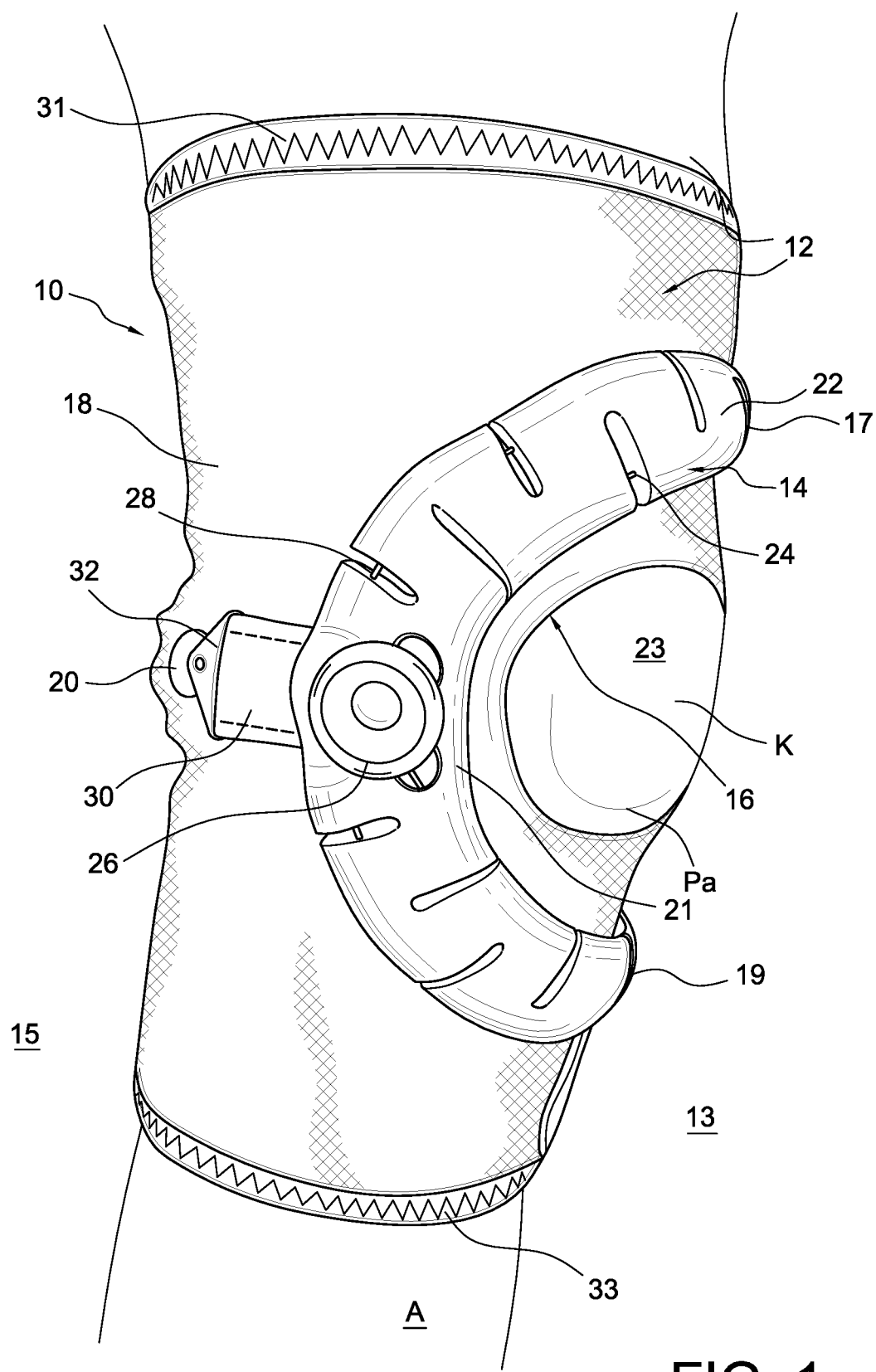
FIG. 1 is a perspective view of one side of a patella device.

A better understanding of different embodiments of the support may be gained from the following description read with the accompanying drawings in which like reference characters refer to like elements.

While the disclosure is susceptible to various modifications and alternative constructions, certain illustrative embodiments are in the drawings and will be described below. It should be understood, however, there is no intention to limit the disclosure to the embodiments disclosed, but on the contrary, the invention covers all modifications, alternative constructions, combinations, and equivalents falling within the spirit and scope of the disclosure and defined by the appended claims.

It will be understood that, unless a term is defined in this disclosure to possess a described meaning, there is no intent to limit the meaning of such term, either expressly or indirectly, beyond its plain or ordinary meaning.

Any element in a claim that does not explicitly state "means for" performing a specified function, or "step for" performing a function, is not to be interpreted as a "means" or "step" clause as specified in 35 U.S.C. § 112, paragraph 6.

B. Environment and Context of Embodiments

The supports and methods for use herein may be used in various articles including braces, medical devices, clothing, apparel, bags, safety restraints and the like. In a preferred embodiment, the supports and methods are described in connection with orthopedic devices.

Numerous orthopedic devices and components (e.g., subshells and strap retainers) for use therewith are described, with particular focus given to braces and components directed to the knee joint and surrounding areas. The orthopedic device embodiments may serve in protective, preventative or remedial capacities. While the orthopedic device is described within the context of a preferred embodiment directed to securing the knee joint, many of the features described may be extended to orthopedic devices and components that secure other joints and body parts, such as the wrist, elbow, shoulder, ankle and neck.

The orthopedic device embodiments and components for use therewith may be dimensioned to accommodate different types, shapes and sizes of human joints and appendages. In addition, embodiments may be modified to orient principal forces exerted by support systems of the embodiments at any desirable location to secure the brace onto a leg to stabilize the knee.

The knee joint comprises two joints, lateral and medial, between the femur and tibia, and one arthrodial joint between the patella and femur. The primary movements of the knee comprise flexion, i.e., rearward rotational movement of the tibia relative to the femur, and extension, i.e., forward rotational movement of the tibia relative to the femur.

For explanatory purposes, each orthopedic device embodiment or component thereof described may be divided into sections denoted by general anatomical terms for the human body. Such anatomical terms are provided to distinguish various elements of the brace embodiments from one another, but which are not to be considered to limit the invention.

Each of these terms may be used regarding a human leg, which is divided in similar sections with a proximal-distal plane generally extending along the meniscus of the knee between the femur and tibia. The terms "proximal" and "distal" generally refer to locations of the brace that correspond to the location of leg relative to the point of attachment of the leg to the body. The terms "upper" and "lower" may be used in combination with "proximal" and "distal" to connote gradations in-location of "proximal" and "distal." The location where the brace corresponds to the knee joint is used to generally delimit the proximal and distal sections of the brace.

The embodiments of the knee brace can also be considered to fall within "anterior" and "posterior" sections by an anterior-posterior plane. The anterior-posterior plane generally corresponds to the coronal or frontal plane of a human leg, which lies along the central longitudinal axis of a body. A posterior side or element is therefore behind this anterior-posterior plane, whereas an anterior side or element is in front of the anterior-posterior plane.

The terms "inwardly" or "inner" are commonly used to distinguish the side of the brace that may be directed to the posterior side of the brace and specifically adjacent to the leg of the wearer of the brace. Contrariwise, the term "outwardly" or "outer" are used to denote the side of the brace opposite to the inwardly side.

The terms "medial" and "lateral" are relative terms generally understood as indicating location near the midsagittal plane or midline. Therefore, elements located near the midline are referred to as "medial" and those elements further from the midline are "lateral." The term "central" is used to denote the area along the midline of a joint dividing and sharing regions of the medial and lateral regions.

In an embodiment of an orthopedic device, regions of the device may fall within the following quadrants: (I) proximal-medial, (II) distal-medial, (III) distal-lateral, and (IV) proximal-lateral. The posterior section of the brace has the following quadrants: (V) proximal-medial, (VI) distal-medial, (VII) distal-lateral, and (VIII) proximal-lateral. Structural members and features thereof will fall within one of the quadrants is specifically referenced in relation to such quadrant, either in its entirety or partially.

The terms "rigid" and "flexible" are repeatedly used to distinguish characteristics of portions of the brace. The term "rigid" should denote that the frame is devoid of flexibility. Within the context of frame members that are "rigid," it should indicate that they might break if bent with sufficient force. The term "flexible" should denote that features are capable of repeated bending. The term "resilient" is used to qualify such flexible features as generally returning to the initially molded shape with permanent deformation.

The anatomical and characteristic terms described herein are not intended to detract from the normal understanding of such terms as readily understood by one of ordinary skill in the art of orthopedics. The elements of the embodiments described should embrace embodiments that generally correspond to the aforementioned anatomical sections. It is understood that the elements of the brace embodiments described may deviate from falling exactly within the confines of the aforementioned anatomical sections.

C. Various Embodiments

Figure 2:
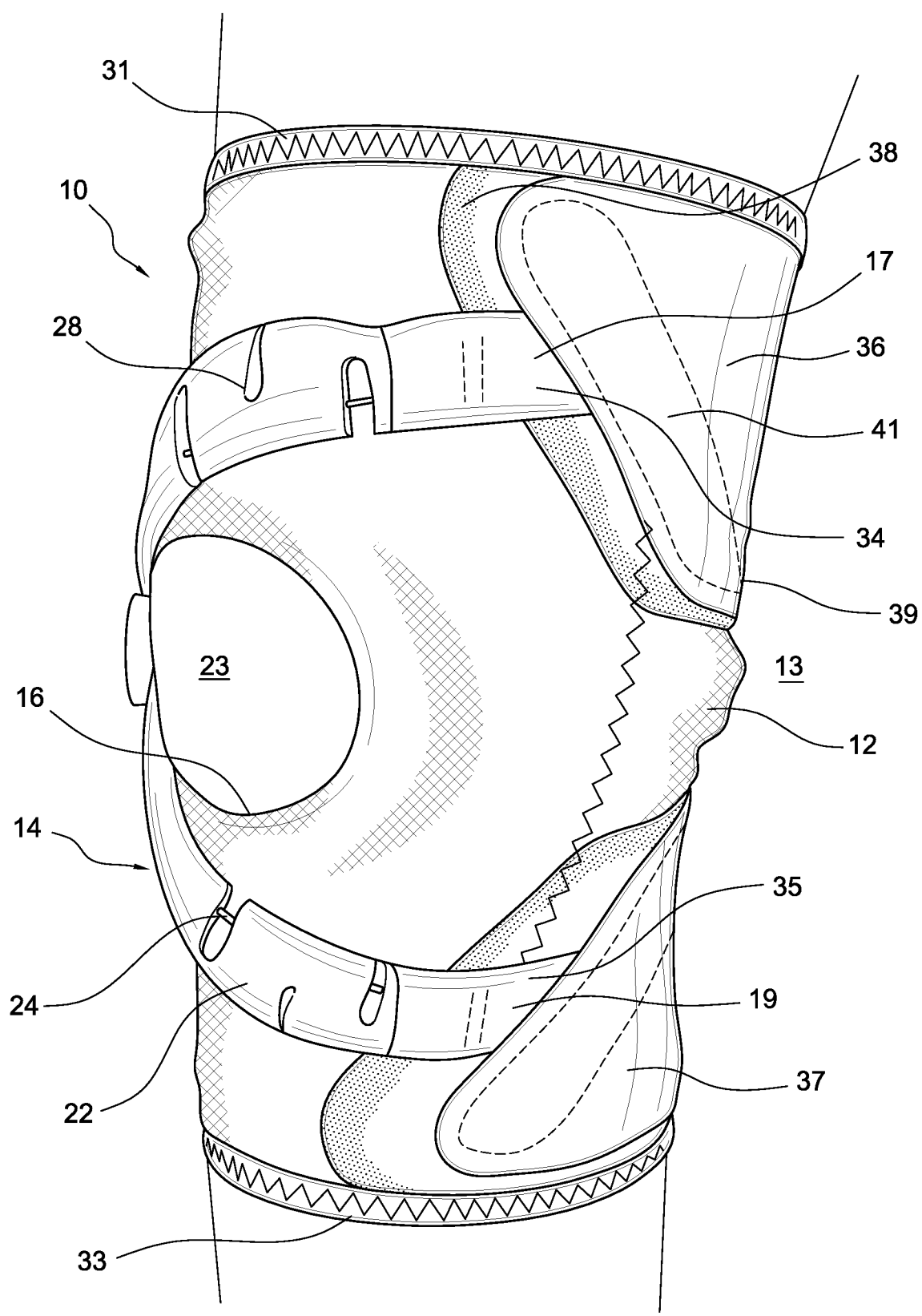
FIG. 2 is a perspective view of another side of the patella device of FIG. 1.

In observing the FIGS. 1 and 2, an embodiment of an orthopedic device is in a patella device 10 for treating a knee K and more particularly a patella Pa of the knee K. The patella device 10 comprises a sleeve 12 defining first and second sides 13, 15 divided by a medial-lateral plane, and a central portion 23 defined along an anterior side "A" of an anterior-posterior plane. A support 14 in the form of a buttress includes a main body 22 having a first end 17 anchored to the first side 13 of the sleeve 12 and a middle portion 21 anchored to the second side of the sleeve 12. The support 14 is located proximate the central portion 23. The central portion 23 may define an opening 16 and the support 14 is arranged to extend across and over the opening 16.

The sleeve 12 is preferably short enabling it to be worn as a stand-alone orthopedic device or in combination with a brace, as depicted in FIG. 7. The sleeve 12 may be constructed from a first section of fabric, such as Lycra, in the anterior area or side, and such fabric may be reinforced to provide rigidity yet is breathable. The posterior area or side may be formed from a second section of fabric, such as Lyrca, that may be thinner or substantially thinner than the first section. The second section is preferably breathable, comfortable permitting each donning and doffing, and a close anatomical fit. The surfaces of the first and second sections preferably have a low friction surface to permit movement of any straps from the orthopedic device.

The support 14 may define an arcuate shape or a C-shape, and is flexible to conform to anatomy of a wearer of the orthopedic device 10. The support 14 is preferably adjustable in length such that a first end 17 of the support 14 includes first and second straps 34, 35 removably securable to a surface of the sleeve 12. The sleeve 12 defines a fastener segment 38 arranged to secure to a corresponding connection feature carried by the first and second straps 34, 35.

The patella device 10 includes first and second flaps 36, 37 each having a first end 39 secured to the sleeve 12 and a second end 41 flexibly extending from the sleeve 12. The second ends 41 are arranged to adjustably secure to an outer surface of the sleeve 12 for adjusting a circumference of the sleeve. The sleeve 12 defines a fastener segment 38 arranged to secure to a corresponding connection feature carried by the first and second straps 34, 35. The second end 41 of the first and second flaps 36, 37 secure to the fastener segment 38.

The flaps 36, 37 may be arranged to secure over and onto the first and second straps 34, 35 and the fastener segment 38. Adjustment of the flaps 36, 37 enable circumferential adjustment of the sleeve to assure it is retained on the leg of the user.

The support 14 may define first and second ends 17, 19 each extending toward the first side 13. The first and second ends 17, 19 have first and second straps 34, 35 securable to the sleeve 12. The middle portion 21 of the support 14 is arranged to resist adjustment of the first and second straps 34, 35. The main body 22 forming the support 14 is preferably formed from a resilient compressible material, such as foam, textile, synthetic or natural rubber, polymer and the like. The elasticity or inelasticity of the material forming the support will depend on the application. In the patella device 10, the support 14 is preferably inelastic to prevent the material of the support from significantly yielding to movement of the user's knee.

Figure 3:
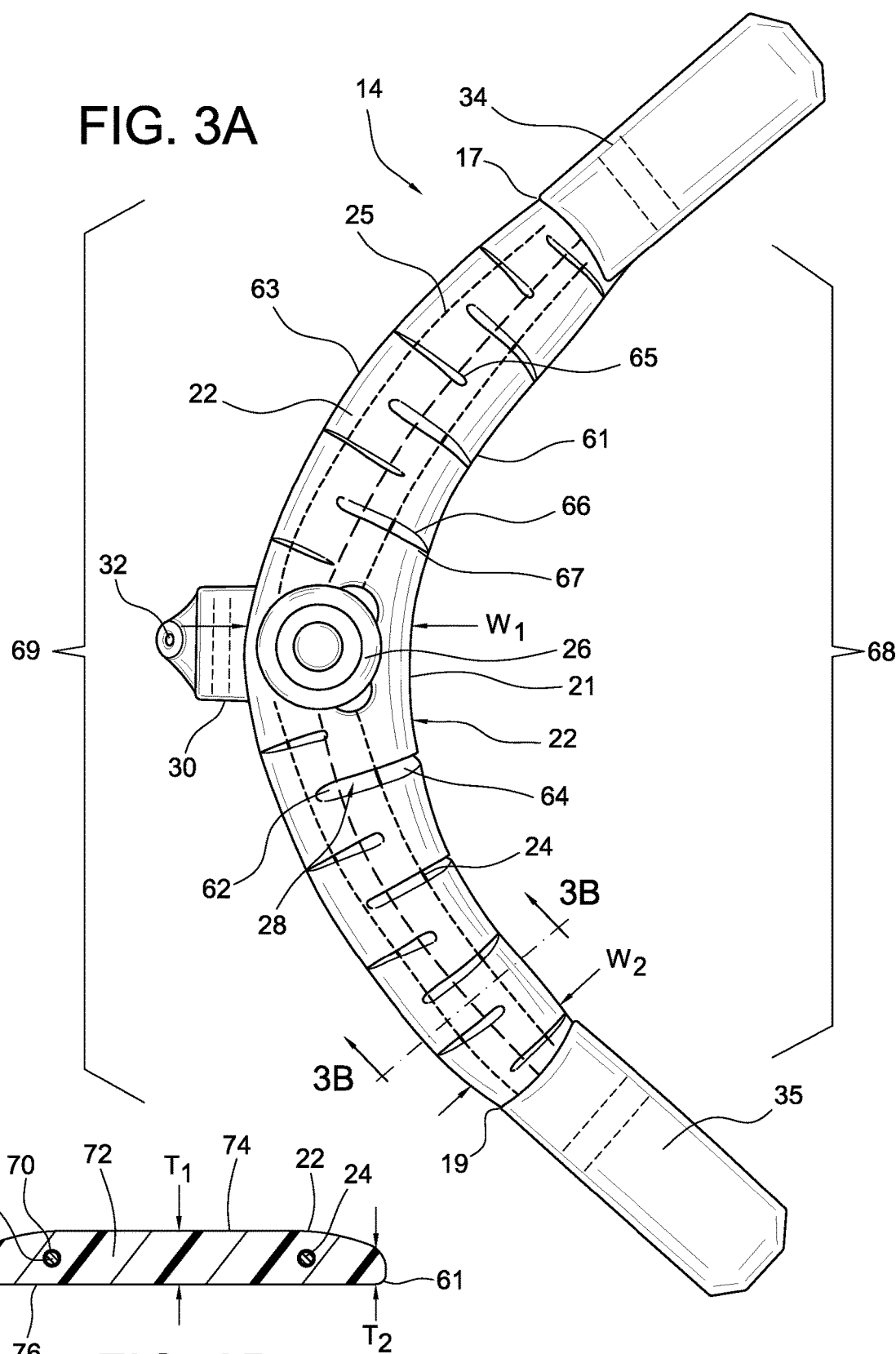
FIG. 3A is a plan view of an embodiment of a support in the patella device of FIG. 1.
FIG. 3B is a cross-section taken along lines 3B-3B in FIG. 3A.

The support may vary in width and thickness over its length or cross-section. For example, in FIG. 3A, the portion of the main body 22 of the support 14 about a tensioning device 26 has a greater width $W_1$ than a width $W_2$ at end portions of the support near the straps 34, 35. This arrangement is to at least accommodate the tensioning device 26 and provide greater support at this section which hugs or embraces a side of the knee. Of course, the widths of the support may be modified for other applications whereby the widths are not limited to a couple of widths but the width may vary along the width according to intended use of the support and the anatomy or other about it extends.

Referring to the thickness, the thickness of the main body 22 may vary along the length of the support 14 and over its cross-section. For example, FIG. 3B shows how the center portion 72 has a greater thickness $T_1$ in part to provide greater rigidity and to accommodate channels 70 through which cable segments 24, 25 extend, as discussed in greater detail below. The thickness $T_2$ at a periphery or edge portions 61, 63 is less than the center portion thickness $T_1$ to provide pressure relief along the periphery.

The main body 22 may be arranged so different surfaces may have varying contours according to desired areas of support and anatomy or other upon which the support extends. For example, FIG. 3B shows a rounded top surface 74 with varying height as a result of the thickness of the support and pressure relieving properties of the periphery. A bottom surface 76 is preferably flat so as secure fully or mostly against the surface upon which the support extends.

Although exemplary widths, thicknesses and surface contours are described, the support is not limited to the depicted examples, but may include any combination and varying properties taking the examples in consideration.

A stay 18 may be at one or both of the first and second sides 13, 15 and extending between first and second ends 31, 33 of sleeve 12. The stay 18 is preferably within the sleeve 12.

Figure 4:
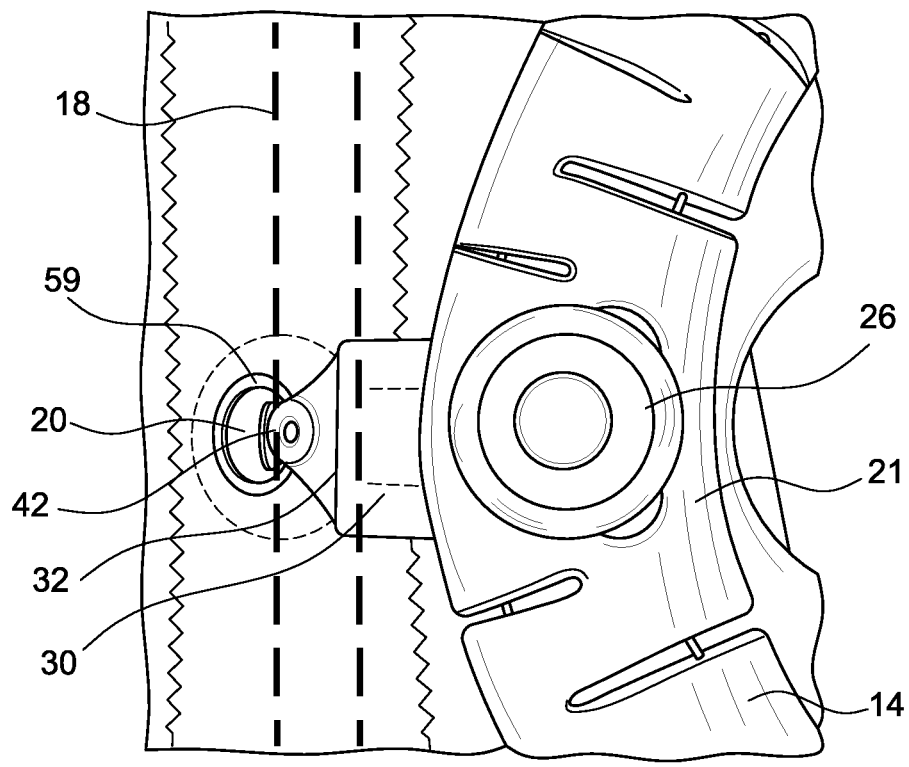
FIG. 4 is a detail view of attachment of a middle portion of the support of FIG. 1 to a sleeve.

According to an embodiment in FIG. 4, the connection assembly 20 includes a locking member 42 carried by the second end 32 of the third strap 30. An anchoring device 59 is carried by the sleeve 12 and arranged for engagement with the locking member 42. FIG. 4 particularly shows the third strap 30 has a first end securing to the middle portion 21 of the support 14 and a second end 32 forms part of a connection assembly 20 for removably coupling the third strap 30 to the sleeve 12. The third strap 30 is preferably inelastic.

As shown in FIGS. 1-3A, the support 14 defines a preferred pattern of openings including at least one opening 28 formed along the length of the support 14 and extending from a periphery 61, 63 into a width of the support 14. The at least one opening 28 preferably extends past a midline or length adjustment axis 65 of the support from the periphery 61, 63.

The at least one opening 28 may be formed as a slit and define first and second ends 62, 64. The first end 62 may extend past the midline 65 short of a first periphery 61, 63 and the second end 64 is defined by opposed side portions 66, 67 clamped against one another depending on the length of the support 14.

According to the variation in FIG. 3A, the main body 22 defines at least one opening 28 formed along a first periphery 61 and at least one opening 28 formed along a second periphery 63 of the support. The at least one opening 28 is defined by a first set of openings 68 formed along a first periphery 61 and a second set of openings 69 formed along a second periphery 63. The first and second openings 68, 69 alternate relative to one another along a length of the support 14.

The tensioning device 26 is preferably secured to the support 14 so actuation of the tensioning device 26 shortens or lengthens a length of the support 14. The a least one cable segment 24, 25 is linked to the tensioning device 26 and cooperates with the support 14 to adjust the length thereof by actuation of the tensioning device 26. The at least one cable segment 24, 25 extends through the thickness of the support 14 and extends from the first end 17 to a second end 19 opposed to the first end 17 such that actuation of the tensioning device 26 adjusts the length of the at least one cable segment 24, 25 to modify the length of the support 14. The support 14 defines at least one opening 28 through which the at least one cable segment 24, 25 extends.

FIG. 3A illustrates the at least one cable as having first and second cables 24, 25 linked to the tensioning device 26 and cooperating with the support 14 to adjust the length thereof by actuation of the tensioning device 26. The first and second cables 24, 25 are on opposed sides of a midline 65 of the support 14.

Various cable types can be used, including but not limited to stranded steel cable with no coating, stranded steel cable with a polymer coating (e.g., nylon coating), monofilament (e.g., nylon), or other suitable elongate elements. In some embodiments, standard conventional shoe laces or textile cords can be used for the cable.

According to the illustrated embodiments, the tensioning device is configured to incrementally provide or release tension to the cable by tensioning. The tensioning device may correspond to a strap tightener assembly for an orthopedic device according to U.S. application Ser. No. 13/739,491, filed on Jan. 11, 2013 and published as U.S. patent application publication no. 2013/0184628 A1 on Jul. 18, 2013. A variation of the tensioning device is also described in U.S. Pat. No. 7,198,610, granted on Apr. 3, 2007, and U.S. Pat. No. 9,125,730, granted Sep. 8, 2015, which are incorporated herein by reference and belong to the assignee of this disclosure. Commercial examples of a tensioning device that may also be used with different embodiments of the support include the BOA lacing system of BOA Technology Inc. of Steamboat Springs, Colo.

The tensioning device is not limited to dial tensioning or a winding system but may include other ratcheting type systems such as a ladder ratchet strap, as discussed in U.S. Pat. No. 7,198,610. Alternatively, the tensioning device can be simplified as a clasp arranged to disengage from the cables and lockingly engage upon a desired tension in the cable by applying traction or wedging. Examples of clasp or blocking devices are described in U.S. Pat. No. 5,566,474, granted Oct. 22, 1996, 7,082,652, granted Aug. 1, 2006, 7,360,282, granted Apr. 22, 2008, each of which are incorporated by reference. From the foregoing, a variety of tensioning devices may be employed in combination with the cable that enable locking of a desired tension in the cable and the selective release of tension of the cable.

Figure 5:
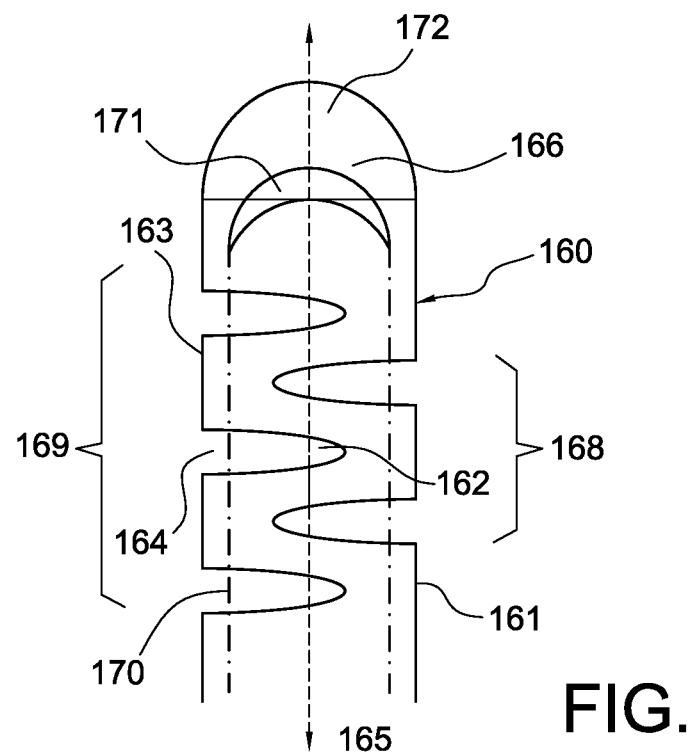
FIG. 5 is a detail view showing an end portion of a support.

FIG. 5 exemplifies another embodiment of an end portion of a support 160 having a similar arrangement to the support 14 in FIG. 3A. The support 160 has a body 166 including first and second patterns of openings 168, 169, along first and second peripheries 161, 162 of the support 160. Each of the openings includes a first end 162 extending past a midline or length adjustment axis 165 extending generally along the midspan of the width of the support 160. A second end 164 is located along one of the peripheries 161, 162. A cable 170 may extend within across the first and second patterns of openings 168,169 to a guide 171 located within or along a surface of the body 166. The body 166 includes a head portion 172 that may be secured directed to an article by suitable fasteners, such as hook-and-loop, buttons, or the like, or may include a strap attached thereto.

In observing FIG. 5, it is preferable that the openings of the first and second patterns overlap one another along the length adjustment axis 165, such that the first ends 162 of the first and second patterns are located along opposed sides of the midline relative to the second ends 164. This arrangement allows the support 160 to both accommodate shape of a surface along which it is located and permits it to shorten or lengthen according to tension adjustment in the cable 170. Length adjustment will occur along the axis of length adjustment 165.

In an alternative, the support may be arranged so that openings do not overlap. While in this alternative the support may not shorten or lengthen according to an increase in tension in the cable, the support can still adapt to a surface along which it is located. A variation of such alternative may include different cables extending along across the openings rather than a cable extending about the guide 171. The cable ends may be anchored at the head portion 172 or other suitable location, and each cable may be adjusted differently so as to create different shape profiles of the first and second peripheries 161, 162.

One of the features the support may have is the overlapping shape described with FIGS. 1-5, so that as cables are adjusted, the support may conform to a surface along which it is located and apply tension thereto. FIGS. 6A-6F depict alternative shape arrangements for the opening patterns, specifically shown as overlapping one another at least to some extent to enable length adjustment of the support.

FIG. 6A shows a support 180 having a pattern of openings in the exemplary form of ellipses 181. At least some of the ellipses overlap 181, particularly along a length adjustment axis 165. The ellipses 181 may occur within peripheries of the support 180, or may be located open along the peripheries as in ellipses 182. The openings may be in an ordered configuration, and are not limited to being in the form of ellipses. The openings may have many shapes providing they enable both shape and length adjustment of the support depending at least one part of adjustment of cables, as described in embodiments herein.

FIG. 6B depicts a support 183 which is a variation of the support 180 in FIG. 6A. The support 183 has random openings 184 in which at least some of the openings overlap one another along the length adjustment axis 165. FIG. 6C shows a support 185 which is another variation of the support 180 in FIG. 6A. The support 185 represents a more narrow width than the support 180, and minimizes the openings 186. A set of openings 186 are generally aligned along the length adjustment axis 165, although openings 187 are located along the peripheries to accommodate shape and length adjustment of the support 185, and yet further openings may be provided.

FIG. 6D depicts a support 188 having a pattern of opening in the exemplary form of a net-type shape whereby the openings are in a predetermined pattern with staggered openings 189 including partial openings 190 along the peripheries of the support 188, but in which the openings 189 overlap at least in part along the length adjustment axis 165.

FIG. 6E shows a support 192 formed from a porous material having openings 193 inherent in the porous material enabling both length and shape adjustment along the length adjustment axis 165. These openings may be micro-holes in an open or closed cell foam such that the micro-holes allow the support to length upon stretching of the support, or collapse upon release of stretching of the support.

FIG. 6F depicts an example of a support 194 having sections 174, 175, 176 with different dimensions. For example, the first section 174 has a height $H_1$ and width $W_3$ greater than a second section 175 with a height $H_2$ and width $W_4$. In this instance, the second section 175 may be a transitory section of the support providing greater bendability but arranged in an area requiring less support. The first section 174 may transition to the second section 175 by a taper profile 177 to enable gradual diminution of support and increased bendability. The support 194 may have a third section 176 having yet a different height H3 and width W6 from the first and second sections 174, 175. Again, any of the sections may be arranged according to desired use of the support, and the support 194 is merely exemplary to show how the support may be modified according to prescribed needs of the support.

The support 194 may likewise have different patterns of openings according to the sections, or may have yet further varying openings within a section itself. The first section 174 is shown with elongate openings 195 generally uniformly spaced apart by height $H_4$, whereas the second section 175 has circular openings 196 spaced apart by height $H_5$ which may be different from height $H_4$. Alternatively, the second section 175 may be devoid of openings so that this region is substantially non-adjustable in height. The third section 176 has openings 197 of differing lengths to cross the length adjustment axis 165, and may be spaced apart differently according to where they are located within the third section 176. For example, some openings are spaced apart by height $H_6$ whereas other openings are spaced apart by height $H_7$ which is different from height $H_6$.

According to the embodiments described herein, a cable system and a tensioning device may be adapted to different configurations. FIGS. 7A-7C exemplify different configurations in which a single or multiple cables are employed and anchored or guided at different locations along the support. While the examples show the support generally having an arcuate or generally perpendicular configuration, the support is not limited to such a shape and may take on the shape of elongate, circular or other shapes.

FIG. 7A shows first and second guides 40, 41 near the first end of the support 14 for redirecting the first and second cable segments 24, 25 of at least one cable 27 to the tensioning device 26. A guide 60 is along a side of the tensioning device 26 and arranged to route the first and second cable segments 24, 25. According to this embodiment, the first and second segments 24, 25 will adjust dependent of one another because of the cable 27. Because the cable 27 "doubles back" at the far ends or at the guides 40, 41 of the support, a doubling effect on the force is generated on the cable 27, similar to a pulley system.

FIG. 7B depicts another cable configuration 120 whereby the cable 121 does not double back as in FIG. 7A. In this configuration, first and second cable segments 124, 126 are independently adjusted by the tensioning device 122 from one another such that the first and second cable segments 124, 126 terminate at first and second anchors 128, 130.

FIG. 7C illustrates another cable configuration 140 in that the cable 141 has first and second cable segments 144, 146 which couple to a tensioning device 142, and terminate and secure to anchors 148, 150. The anchors 148, 150 may be proximate to the tensioning device 142, and the first and second cable segments 144, 146 extend about guides 152, 154 so the cable "doubles back." In this configuration, while there is a doubling of the force generate when the cable 141 is tensioned, the first and second cable segments are generally independent of one another.

In any of the cable configurations, the tensioning device is not limited to being centrally located along the cable configuration but may be located so the initial lengths of the first and second cable segments are disproportionate relative to one another to achieve different contouring and tensioning of each of the first and second cable segments. By placing the tensioning device generally in the middle of the cable configuration, the support may probably have a generally uniform contraction. Alternatively, by disproportionately placing the tensioning device in the cable configuration, there may be non-uniform contraction so the shape of the support may contort.

The cable configuration is not limited to a single tensioning device, however it is envisioned that multiple cables may be employed that are respectively tensioned independently from one another by their own or shared tensioning devices. Additionally, while the cable configurations schematically show the cable as generally linearly extending through or relative to the body of the support, the cable may be arranged so that it alternates between opposed sides of the length adjustment axis, either terminating at an anchor or returning toward or to the tensioning device much like lacing of shoes.

While the cable is described as extending through the body of the support in certain embodiments, it may be located along at least one of the surfaces of the body with external guides channeling the course of the cable. Alternatively, the support body may define channels within the thickness of the body through which the cable extends. Essentially, the cable configuration is arranged so that adjusting a length of the cable relative to the support enables length adjustment and/or shape contouring of the support, whether the cable is internally or externally mounted relative to the support.

From these cable configurations and the aforementioned embodiments, a method for adjusting a length involves adjusting tension in the at least one cable or cable segments by regulating the tensioning device and causing geometry of the at least one opening to modify according to tension in the cable. Ends of the support are preferably anchored at first and second locations such that the length of the support adjusts along the length adjustment axis according to regulation of the tensioning device. By providing at least one peripheral opening along a periphery of the support, the shape of the support may be contoured according to regulation of the tensioning device by modifying a geometry of the peripheral opening as a result in adjustment of tension in the at least one cable.

Figure 8:
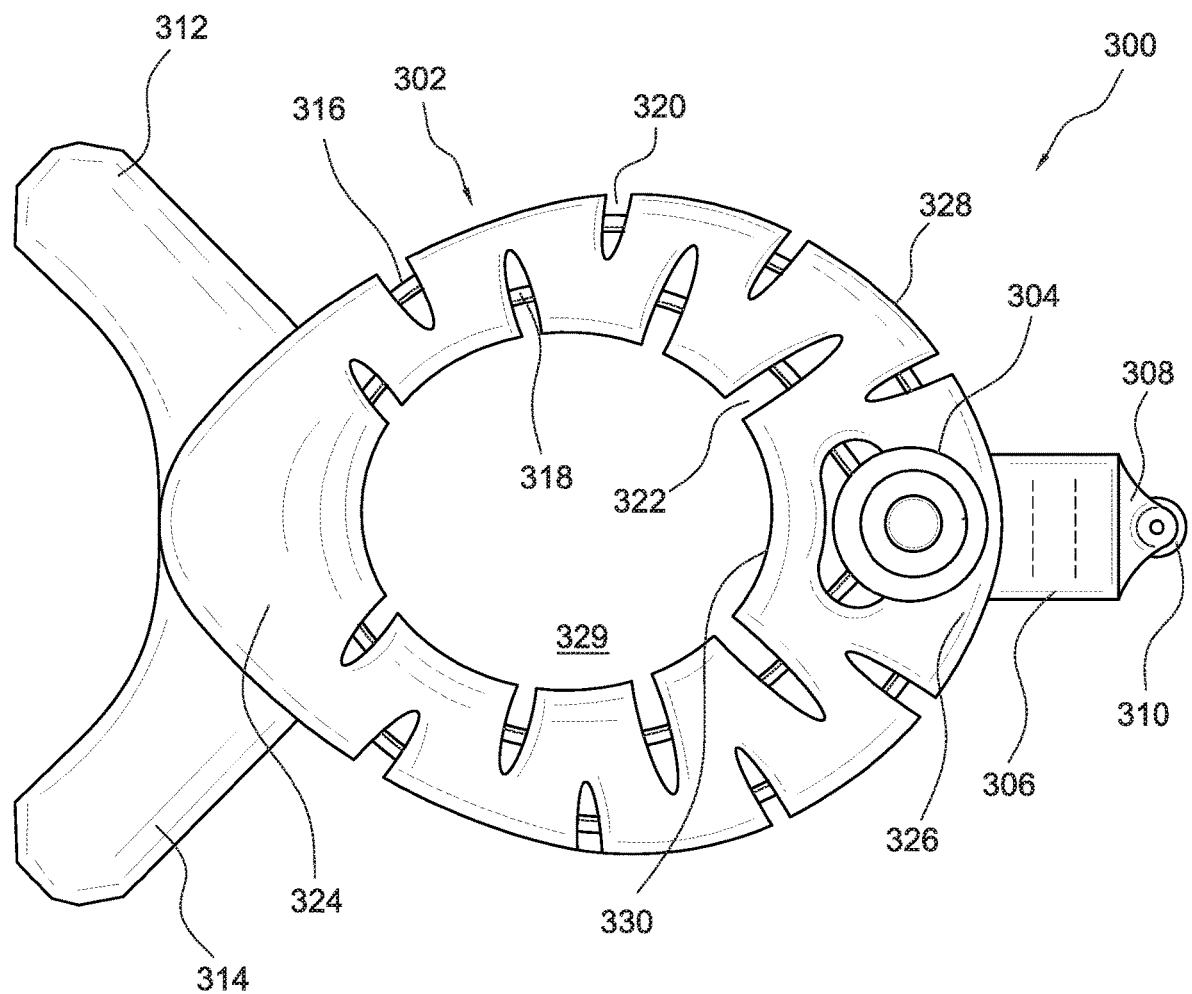
FIG. 8 is a plan view of another embodiment of a support for the patella device of FIG. 1.

FIG. 8 illustrates another embodiment of a support 300 having a main body 302 generally forming a circular or oval profile, particularly an opening 329 for securing about a patella as in FIG. 1. For example, the inner profile 330 of the main body 302 is circular, and the outer profile 328 is generally in a tear drop shape such that a first end 324 is tapered whereas a second end 326 is rounded. The tear drop shape caters to the first and second straps 312, 314 located at the first end 324 to facilitate securing to the sleeve, as in FIG. 1. The rounded shape at the second end 326 is arranged to accommodate the tensioning device 304 and the third strap 306.

As with the embodiment of FIGS. 1-4, the third strap 306 includes an anchor 308 and a locking member 310 such as a pin or other connector to the sleeve. One or multiple cables 316, 318 may be included in the main body 302 and coupled to the tensioning device 304.

The shape of the main body 302 may vary depending on the tension of the cables 316, 318 such that the opening 329 may be elongate, whereas reducing the tension will cause the opening 329 to reflect a more circular profile. As with the embodiment of FIGS. 1 and 2, the at least one opening in the form of slits 320, 322 may open or close to accommodate the shape of the support depending on the displacement of the cables 316, 318. The first and second ends 324, 326 are preferably devoid of the slits 320, 322 to reinforce the straps and serve as anchor portions of the main body 302 counteracting tension or securement of the straps.

Figure 9:
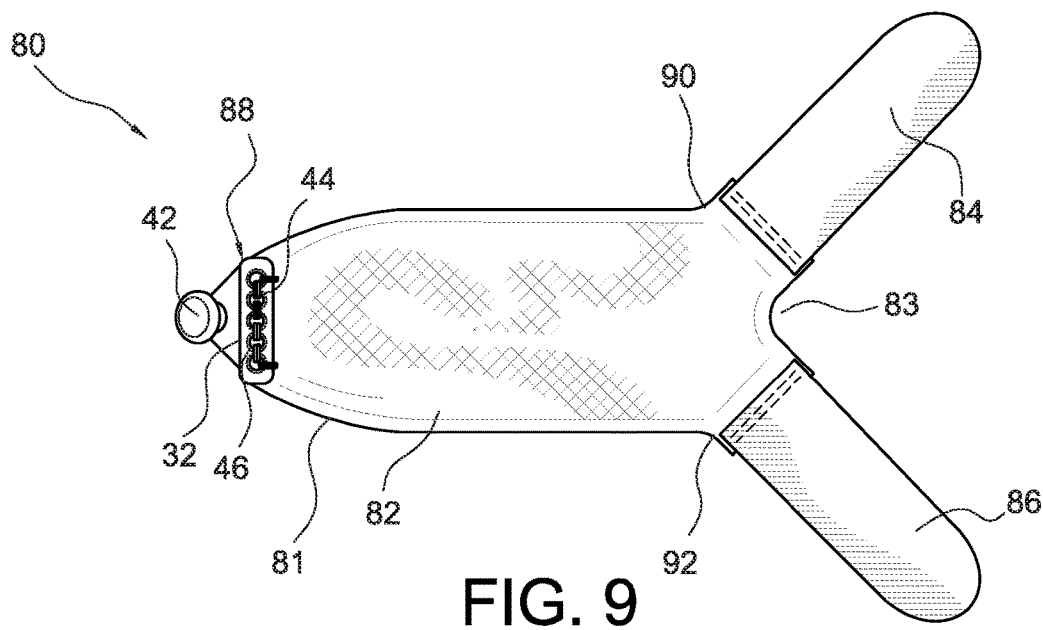
FIG. 9 is a plan view of another embodiment of a support for the patella device of FIG. 1.

FIG. 9 shows an alternative embodiment of a support 80. The support 80 includes an elongate body 82 defining a first end 81 including a connection assembly 88 for securing to the sleeve 12. A second end is bifurcated into first and second portions 90, 92 each carrying a strap 84, 86 arranged to secure to the sleeve 12 of FIGS. 1 and 2. The elongate body 82 is preferably elastic and extends over the opening 23 of the sleeve to secure the patella.

In this embodiment, a rear surface of the elongate body 82 may include silicone to assist in maintaining the support 80 in position over the knee. The strap is particularly used to exert a downward force on the patella and a lateral to medial pull. As with any of the embodiments, the connection assembly 88 may be secured to the elongate body 82 by stitching 44 extending through a plurality of apertures 46 formed by the connection assembly 88.

Figure 10:
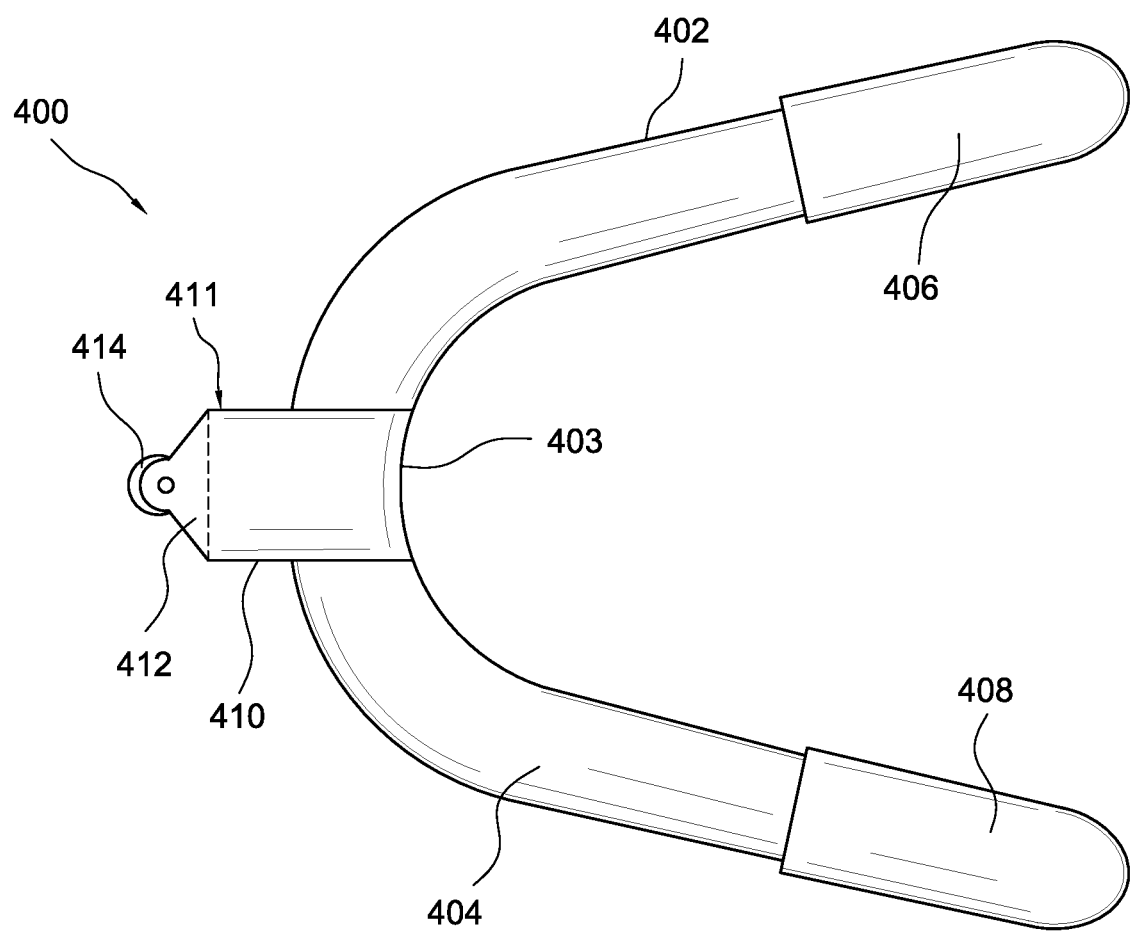
FIG. 10 is a plan view of another embodiment of a support for the patella device of FIG. 1.

FIG. 10 is another embodiment illustrating a support 400. The support 400 includes first and second portions 402, 404 extending from a main portion 403. The support 400 generally forms a U-shape subject to deformation according to actual use of the support. The first and second portions 402, 404 include fastener tabs 406, 408 for securing to the sleeve 12. A connection assembly 411 secures to the main portion 403 and includes a strap 410 and an anchor 412 with a locking member 414 for connecting to the sleeve similarly to the embodiment of FIG. 1.

Figure 11:
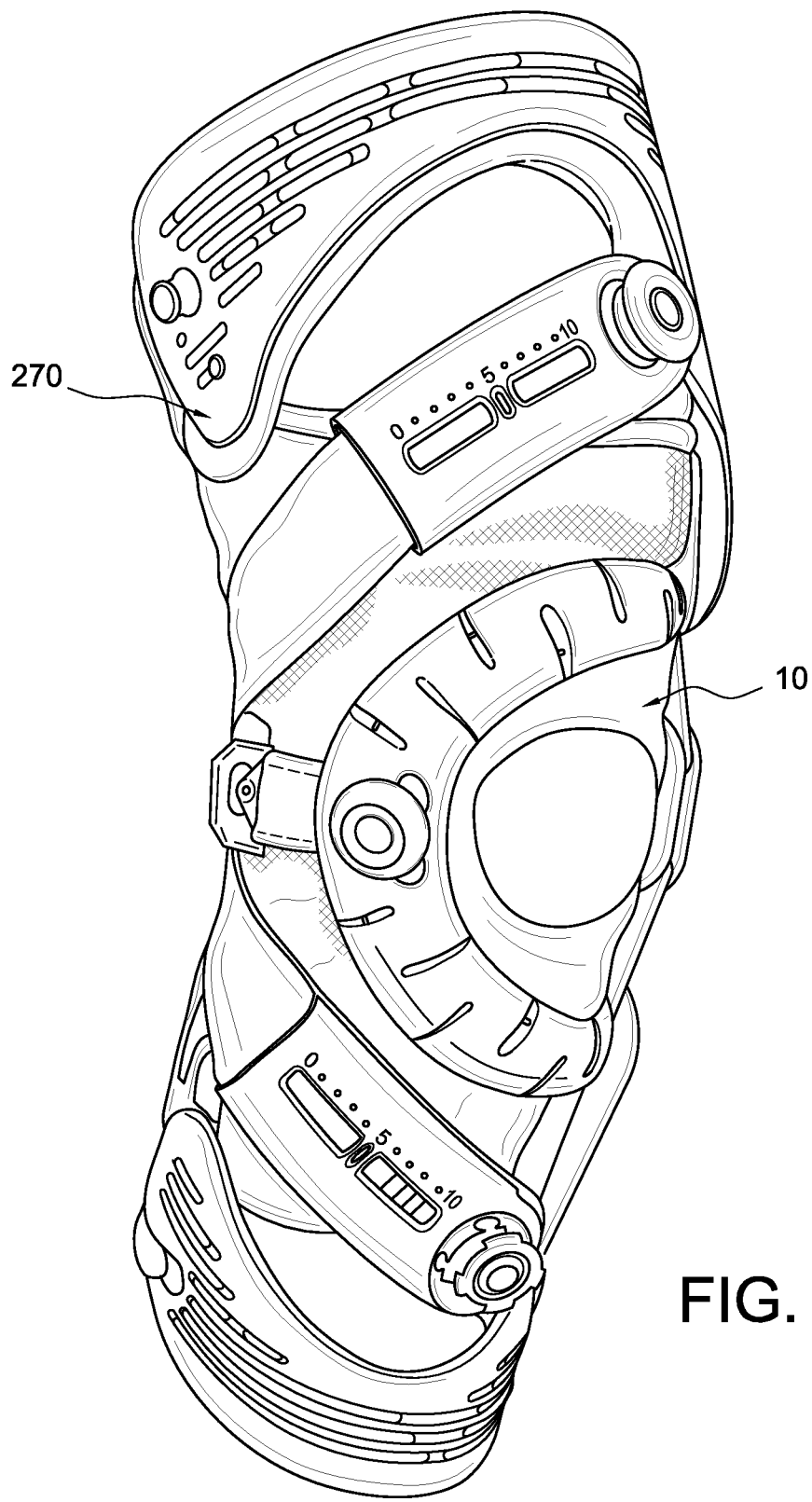
FIG. 11 is a perspective view of the patella device in combination with an orthopedic device.

FIG. 11 shows the patella device 10 in use with an orthopedic device 270. Although other orthopedic devices are envisioned, an example of a suitable orthopedic device may be found in U.S. Pat. No. 7,198,610.

Figure 12:
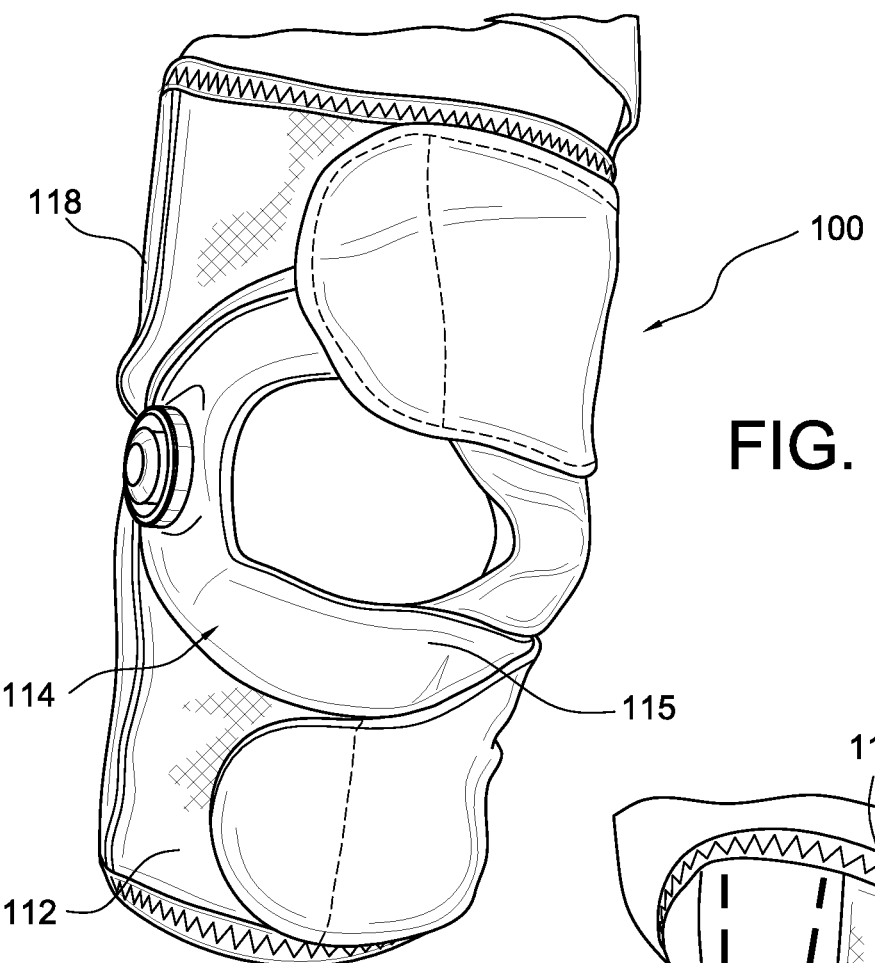
FIG. 12 is a perspective front view of another embodiment of a patella device.
Figure 13:
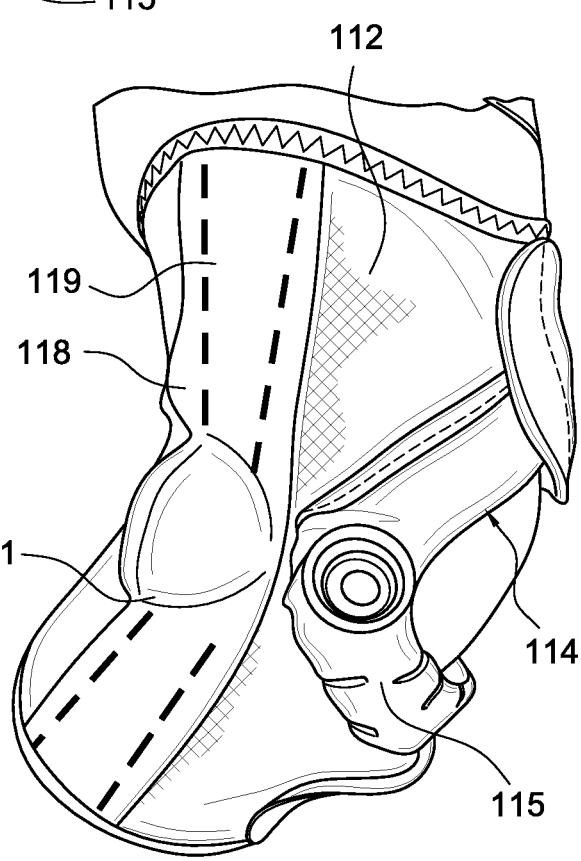
FIG. 13 is a perspective side view of the patella device of FIG. 12.

FIGS. 12 and 13 illustrate an alternate embodiment of a patella device 100. The patella device 100 includes a sleeve 102 arranged to secure over a user's leg similarly arranged as the embodiment of FIG. 1. The support 114 is covered by a covering 115 adapted to accommodate movement of the support as it expands or contracts due to tensioning of cables therein, as in the embodiment of FIG. 1. FIG. 13 shows how a hinge 121 and corresponding struts 119 may be located within or concealed by the sleeve 112 by a covering 118.

Figure 15:
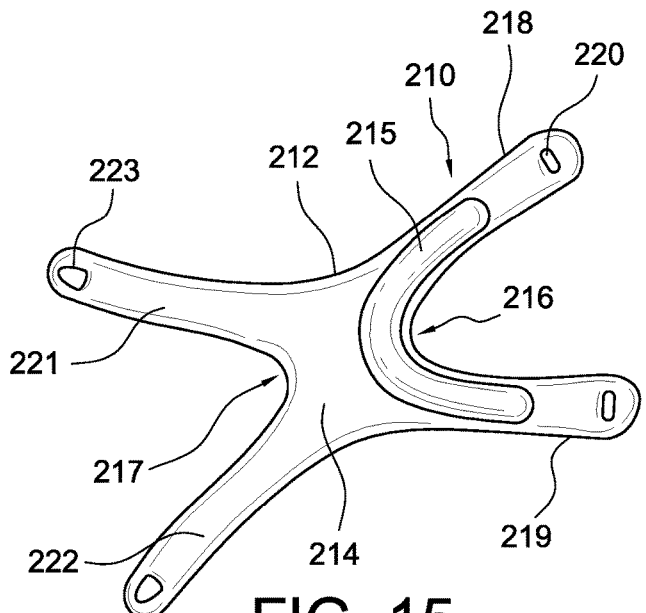
FIG. 15 is a perspective front view of the patella device of FIG. 14 in an orthopedic device.
Figure 14:
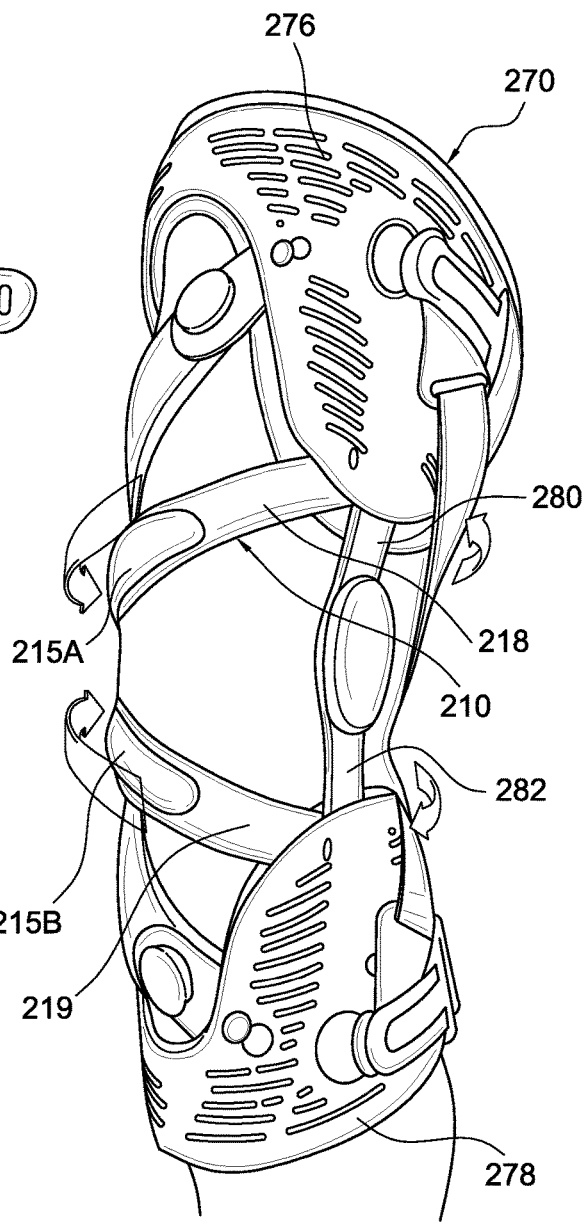
FIG. 14 is a perspective view of another embodiment of a patella device.
Figure 16:
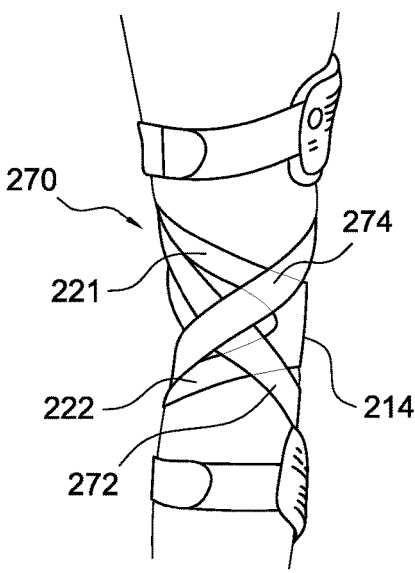
FIG. 16 is a perspective rear view of the patella device of FIG. 15 in the orthopedic device of FIG. 14.

FIGS. 14-16 depict another alternate embodiment of a patella device 210 for use with an unloading brace 270 with a strap assembly having dynamic force straps 272, 274. The patella device 210 includes a main body 212 defining a central portion 214 and first and second side portions 216, 217. The first side portion 216 includes bifurcated first and second extensions 218, 219. A support 215 secures to the first side 216 and extends along the first and second extensions 218, 219.

The first and second extensions 218, 219 include connection elements 220 for securing to the orthopedic device 270 at frame supports 276, 278 spaced apart by struts 280, 282. The second side portion 217 includes bifurcated first and second extensions 221, 222. The first and second extensions 221, 222 of the second side 217 include connection elements 223, and may extend over or underneath the strap assembly 272, 274 supported by the unloading device 270.

Figure 17:
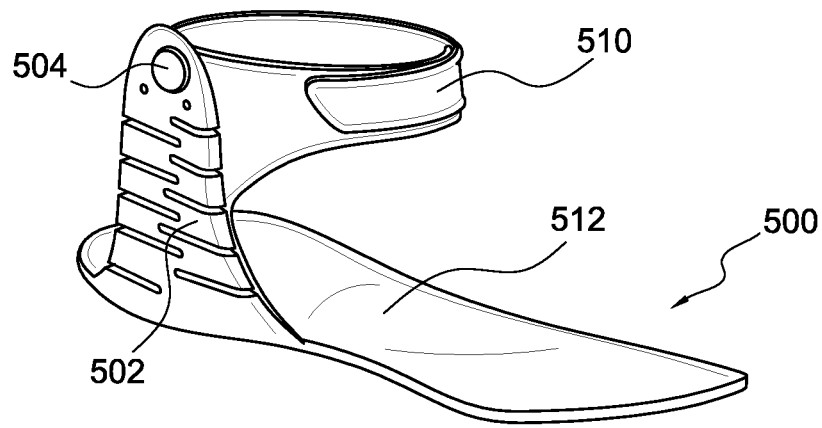
FIG. 17 is a perspective view of an ankle brace having a support.
Figure 18:
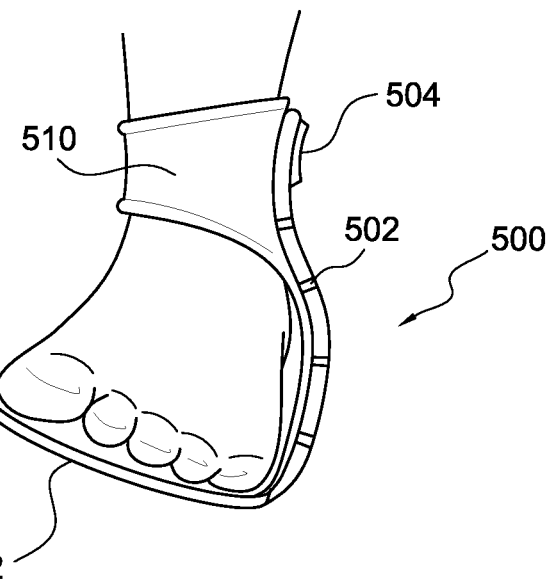
FIG. 18 is a front view of an ankle brace of FIG. 17.
Figure 19:
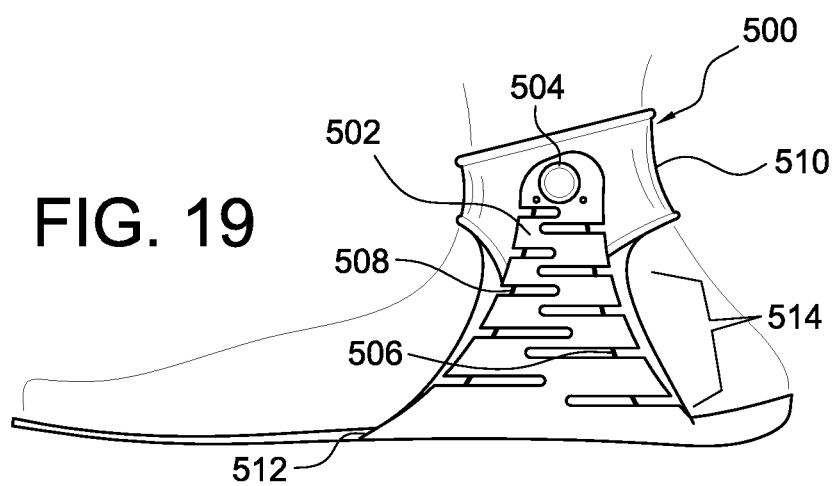
FIG. 19 is a side view of an ankle brace of FIG. 17.

Referring to FIGS. 17 to 19, an ankle brace 500 is arranged with an ankle support 502 attached to an ankle brace 510 adapted for adjusting an angle of a user's ankle for inversion and eversion control of an ankle. The brace 500 includes a foot plate or foot portion 512 and an upper portion 510 connectable above a user's ankle. The support 502 is located between or at the upper portion 510 and the foot plate 512. The support 502 has openings 506 and is adjustable by a tensioning device 504 secured to a cable 508 in a manner according to any of the aforementioned configurations. A distance 514 of the support 502 between the upper portion 510 and the foot plate 512 is adjustable in length and angle according to adjustment of the tensioning device.

The support may be constructed of a material that is substantially rigid or becomes sufficiently rigid to place and maintain an ankle in a desired eversion or inversion configuration according adjustment by the tensioning device. The support may be sufficiently compressible to enable comfort to the user's ankle as the support is adjusted. The shape or geometry of the support may be adapted for contouring to a user's ankle such in the illustrated example whereby the width of the support tapers from the foot plate to the upper portion.

The embodiments of the support described above in accordance with the present disclosure reduce pain, speed healing processes, and impart improved stability and mobility in numerous indications. In an orthopedic device, for example, the support permits more precise adjustment and enables efficient coordination between a medical professional and the wearer on the degree the orthopedic device should be configured. Patient comfort is also enhanced and donning and doffing of the orthopedic device is eased with the novel features described.

It is to be understood that not necessarily all such objects or advantages may be achieved under any embodiment of the disclosure. Those skilled in the art will recognize that the support, either by itself or combined with another article such as an orthopedic device, may be embodied or carried out in a manner that achieves or optimizes one advantage or group of advantages as taught without achieving other objects or advantages as taught or suggested.

The skilled artisan will recognize the interchangeability of various features from different embodiments. Besides the variations described, other known equivalents for each feature can be mixed and matched by one of ordinary skill in this art to construct a support or an orthopedic device under principles of the present disclosure.

Although the support has been disclosed in certain preferred embodiments and examples, it therefore will be understood by those skilled in the art that the present invention extends beyond the specifically disclosed embodiments to other alternative embodiments and/or uses of the support and obvious modifications and equivalents thereof. It is intended that the present disclosure should not be limited by the particular disclosed embodiments described above.

The invention claimed is:

1. A support, comprising:
   a body having a first portion, a second portion and a middle portion separating the first and second portions, the body defining a length adjustment axis;
   a tensioning device connected to the support wherein adjustment of the tensioning device shortens or lengthens a length of the support at least through the middle portion along the length adjustment axis;
   a first attachment extending from a first end at the first portion of the body and generally parallel therewith; and
   a second attachment extending from a second end at the second portion of the body and generally parallel therewith.

2. The support of claim 1, further comprising at least one cable linked to the tensioning device and extending through a thickness of the body from the first portion to the second portion of the body such that actuation of the tensioning device adjusts a length of the body.

3. The support of claim 2, wherein the thickness of the body consists between top and bottom surfaces of the body, the body forming a channel within the thickness of the body and being located at a center portion of the body through which the at least one cable extends.

4. The support of claim 2, wherein the body defines at least one opening overlapping at least part of the length adjustment axis such that length adjustment is governed by modification of a size of the at least one opening according to adjustment by the tensioning device.

5. The support of claim 2, wherein the body defines at least one opening formed along the length of the support and extending from a periphery into a width of the support, a channel being defined on opposed sides of the at least one opening and the at least one cable extending between and within the at least one opening.

6. The support of claim 5, wherein the at least one opening extends past the length adjustment axis of the support from the periphery, the length adjustment axis being defined along a midline of the body.

7. The support of claim 5, wherein the at least one opening defines first and second ends, the first end extending past the length adjustment axis short of a first periphery and the second end defined by opposed side portions arranged to clamp against one another depending on the length of the support, the length adjustment axis being defined along a midline of the body.

8. The support of claim 1, wherein a thickness of the body varies along the length adjustment axis.

9. A method for adjusting a length of a support having a body having a first portion, a second portion and a middle portion separating the first and second portions, the body defining a length adjustment axis; a tensioning device connected to the support wherein adjustment of the tensioning device shortens or lengthens a length of the support at least through the middle portion along the length adjustment axis; a first attachment extending from a first end at the first portion of the body and generally parallel therewith; and a second attachment extending from a second end at the second portion of the body and generally parallel therewith;
   wherein the body has at least one opening defining a predetermined geometry and overlapping at least part of a length adjustment axis, at least one cable operatively being engaged to the tensioning device, the method comprising the steps of:
   adjusting tension in the at least one cable by regulating the tensioning device and causing geometry of the at least one opening to modify according to tension in the cable.

10. The method of claim 9, wherein the at least one opening overlaps at least part of the length adjustment axis such that length adjustment is governed by modification of a size of the at least one opening according to adjustment by the tensioning device.

11. The method of claim 9, further comprising the step of:
    anchoring first and second ends of the support to first and second locations, the length of the support adjusting along the length adjustment axis according to regulation of the tensioning device.

12. The method of claim 9, further comprising the steps of:
    providing at least one peripheral opening along a periphery of the support;
    contouring a shape of the support according to regulation of the tensioning device by modifying a geometry of the peripheral opening as a result in adjustment of tension in the at least one cable.

13. The method of claim 9, further comprising the step of attaching the support to an orthopedic brace, a first end of the support securing to the orthopedic device and a second end of the support securing to the orthopedic device, with a middle portion located between the first and second ends adapted to move relative to the first and second ends along the length adjustment axis.

14. The method of claim 13, further comprising the step of attaching the middle portion to the orthopedic brace.

15. The method of claim 14, wherein a strap extends from the middle portion and secures to the orthopedic device.

16. The method of claim 15, wherein the strap is inelastic.

17. The method of claim 9, wherein the body consists a resiliently compressible material and having a first portion, a second portion and a middle portion separating the first and second portions, the body defining a length adjustment axis.

18. The method of claim 17, wherein the resiliently compressible material is inelastic, wherein the resiliently compressible material is foam.

* * * * *